US010539582B2

(12) United States Patent
Okamoto et al.

(10) Patent No.: US 10,539,582 B2
(45) Date of Patent: Jan. 21, 2020

(54) SUBSTRATE FOR SAMPLE ANALYSIS, SAMPLE ANALYSIS DEVICE, SAMPLE ANALYSIS SYSTEM, AND METHOD FOR REMOVING LIQUID FROM LIQUID THAT CONTAINS MAGNETIC PARTICLES

(71) Applicant: PHC HOLDINGS CORPORATION, Tokyo (JP)

(72) Inventors: Fusatoshi Okamoto, Ehime (JP); Masahiro Johno, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 186 days.

(21) Appl. No.: 15/323,007

(22) PCT Filed: Jun. 29, 2015

(86) PCT No.: PCT/JP2015/068723
§ 371 (c)(1),
(2) Date: Dec. 29, 2016

(87) PCT Pub. No.: WO2016/002728
PCT Pub. Date: Jan. 7, 2016

(65) Prior Publication Data
US 2017/0131305 A1   May 11, 2017

(30) Foreign Application Priority Data

Jun. 30, 2014   (JP) ................................. 2014-134778

(51) Int. Cl.
*G01N 35/00*   (2006.01)
(52) U.S. Cl.
CPC . *G01N 35/00069* (2013.01); *G01N 35/00584* (2013.01); *G01N 2035/00495* (2013.01)
(58) Field of Classification Search
None
See application file for complete search history.

(56) References Cited

U.S. PATENT DOCUMENTS

| | | | |
|---|---|---|---|
| 4,495,295 A | 1/1985 | Neurath | |
| 4,673,653 A | 6/1987 | Guigan | |
| 4,745,077 A | 5/1988 | Holian et al. | |
| 4,916,081 A | 4/1990 | Kamada et al. | |
| 4,918,025 A | 4/1990 | Grenner | |
| 4,990,075 A | 2/1991 | Wogoman | |
| 5,160,702 A | 11/1992 | Kopf-Sill et al. | |
| 5,173,262 A | 12/1992 | Burtis et al. | |
| 5,466,574 A | 11/1995 | Liberti et al. | |
| 5,627,041 A | 5/1997 | Shartle | |
| 5,741,714 A | 4/1998 | Liberti | |
| 5,912,134 A | 6/1999 | Shartle | |
| 6,063,589 A * | 5/2000 | Kellogg | B01F 13/0059 366/DIG. 3 |
| 6,103,537 A | 8/2000 | Ullman et al. | |
| 6,238,538 B1 | 5/2001 | Parce et al. | |
| 6,274,384 B1 | 8/2001 | Starzl et al. | |
| 6,458,553 B1 | 10/2002 | Colin et al. | |
| 6,551,841 B1 * | 4/2003 | Wilding | B01F 15/0264 422/400 |
| 7,476,543 B2 * | 1/2009 | Becker | G01N 1/2813 422/561 |
| 7,867,753 B2 * | 1/2011 | Andersson | B01L 3/508 435/287.1 |
| 7,897,398 B2 | 3/2011 | Saiki | |
| 8,058,010 B2 * | 11/2011 | Erickson | G01N 35/00009 435/288.3 |
| 8,415,140 B2 | 4/2013 | Saiki et al. | |
| 8,703,070 B1 * | 4/2014 | Parng | B01L 3/5025 422/407 |
| 8,956,879 B2 | 2/2015 | Tanaka et al. | |
| 2002/0019059 A1 | 2/2002 | Chow et al. | |
| 2002/0071788 A1 | 6/2002 | Fujii et al. | |
| 2002/0119482 A1 | 8/2002 | Nelson et al. | |
| 2002/0137218 A1 | 9/2002 | Mian et al. | |
| 2002/0151078 A1 | 10/2002 | Kellogg et al. | |

(Continued)

FOREIGN PATENT DOCUMENTS

EP   0326100 A2   8/1989
EP   0724156 A1   7/1996

(Continued)

OTHER PUBLICATIONS

International Search Report issued in corresponding International Patent Application No. PCT/JP2015/068729, dated Sep. 1, 2015; with English translation.

(Continued)

*Primary Examiner* — Ann Y Lam
(74) *Attorney, Agent, or Firm* — McDermott Will & Emery LLP

(57) ABSTRACT

A substrate for sample analysis on which transfer of a liquid is to occur with rotational motion includes: a substrate having a rotation axis; a first chamber being located in the substrate and having a first space for retaining a liquid and magnetic particles; a second chamber being located in the substrate and having a second space for retaining the liquid to be discharged from the first chamber; a channel being located in the substrate and having a path connecting the first chamber and the second chamber; and a magnet being located in the substrate and near the first space in the substrate for capturing the magnetic particles in the first chamber.

3 Claims, 17 Drawing Sheets

(Continued)

(56) References Cited

U.S. PATENT DOCUMENTS

| | | | |
|---|---|---|---|
| 2002/0180975 A1* | 12/2002 | Ogura | G01N 21/13 356/445 |
| 2003/0026740 A1 | 2/2003 | Staats | |
| 2003/0077204 A1 | 4/2003 | Seki et al. | |
| 2003/0138819 A1 | 7/2003 | Gong et al. | |
| 2003/0211010 A1 | 11/2003 | Nagaoka et al. | |
| 2004/0089616 A1 | 5/2004 | Kellogg et al. | |
| 2004/0137607 A1* | 7/2004 | Tanaami | B01L 3/502715 435/287.2 |
| 2004/0181343 A1* | 9/2004 | Wigstrom | B01L 3/5027 702/19 |
| 2005/0079634 A1 | 4/2005 | Wilding et al. | |
| 2005/0123447 A1 | 6/2005 | Koike et al. | |
| 2005/0178218 A1* | 8/2005 | Montagu | B01L 3/50273 73/864.34 |
| 2005/0221281 A1 | 10/2005 | Ho | |
| 2005/0287577 A1 | 12/2005 | Yamamichi | |
| 2006/0061760 A1 | 3/2006 | Matsumoto et al. | |
| 2006/0263242 A1 | 11/2006 | Yang et al. | |
| 2006/0292641 A1 | 12/2006 | Nakanishi et al. | |
| 2007/0141576 A1* | 6/2007 | Koide | B01L 3/508 435/6.14 |
| 2007/0160979 A1* | 7/2007 | Andersson | B01L 3/508 435/5 |
| 2007/0166721 A1 | 7/2007 | Phan et al. | |
| 2007/0189927 A1 | 8/2007 | Ballhorn et al. | |
| 2007/0218566 A1 | 9/2007 | Barten et al. | |
| 2007/0224304 A1* | 9/2007 | Kunimatsu | B29C 45/062 425/150 |
| 2007/0243111 A1 | 10/2007 | Momose | |
| 2007/0266777 A1 | 11/2007 | Bergman et al. | |
| 2008/0035579 A1 | 2/2008 | Lee et al. | |
| 2008/0073546 A1 | 3/2008 | Andersson et al. | |
| 2008/0102537 A1 | 5/2008 | Harding et al. | |
| 2008/0131978 A1 | 6/2008 | Fujimura et al. | |
| 2008/0138831 A1 | 6/2008 | Hataoka | |
| 2008/0156079 A1 | 7/2008 | Momose | |
| 2008/0171400 A1 | 7/2008 | Cho et al. | |
| 2008/0176272 A1 | 7/2008 | Bergman et al. | |
| 2008/0219891 A1 | 9/2008 | McDevitt et al. | |
| 2008/0240996 A1 | 10/2008 | Harding et al. | |
| 2008/0242556 A1 | 10/2008 | Cao et al. | |
| 2009/0042317 A1 | 2/2009 | Ikeda | |
| 2009/0053108 A1 | 2/2009 | Cho et al. | |
| 2009/0111190 A1 | 4/2009 | Andersson et al. | |
| 2009/0123337 A1 | 5/2009 | Noda et al. | |
| 2009/0126516 A1* | 5/2009 | Yamamoto | B01F 13/0071 73/864.22 |
| 2009/0155125 A1 | 6/2009 | Michiue et al. | |
| 2009/0169430 A1 | 7/2009 | Yamamoto et al. | |
| 2009/0253130 A1* | 10/2009 | Yoo | B01F 13/0059 435/6.11 |
| 2009/0317896 A1 | 12/2009 | Yoo | |
| 2010/0071486 A1 | 3/2010 | Kim et al. | |
| 2010/0074801 A1 | 3/2010 | Saiki | |
| 2010/0078322 A1 | 4/2010 | Yamanishi et al. | |
| 2010/0132820 A1 | 6/2010 | Ozaki et al. | |
| 2010/0151560 A1 | 6/2010 | Wo et al. | |
| 2010/0159600 A1 | 6/2010 | Shin et al. | |
| 2010/0184228 A1 | 7/2010 | Saiki | |
| 2010/0221741 A1 | 9/2010 | Saiki et al. | |
| 2010/0255589 A1 | 10/2010 | Saiki et al. | |
| 2010/0262389 A1 | 10/2010 | Nakanishi et al. | |
| 2010/0281961 A1 | 11/2010 | Saiki et al. | |
| 2010/0290955 A1 | 11/2010 | Cho et al. | |
| 2011/0045505 A1 | 2/2011 | Warthoe et al. | |
| 2011/0058985 A1 | 3/2011 | Saiki et al. | |
| 2011/0117665 A1* | 5/2011 | Saiki | B01L 3/502715 436/164 |
| 2011/0124128 A1 | 5/2011 | Oosterbroek et al. | |
| 2011/0126646 A1* | 6/2011 | Saiki | G01N 1/38 73/864.81 |
| 2011/0250695 A1 | 10/2011 | Sarofim et al. | |
| 2012/0024083 A1 | 2/2012 | Wo et al. | |
| 2012/0135533 A1 | 5/2012 | Shikida et al. | |
| 2012/0244607 A1 | 9/2012 | Iwamoto et al. | |
| 2012/0261256 A1 | 10/2012 | Chang et al. | |
| 2012/0269701 A1 | 10/2012 | Linder et al. | |
| 2012/0275971 A1* | 11/2012 | Momose | B01L 3/5027 422/502 |
| 2012/0322683 A1 | 12/2012 | Liu et al. | |
| 2013/0029361 A1 | 1/2013 | Hamachi et al. | |
| 2013/0074962 A1 | 3/2013 | Garcia da Fonseca et al. | |
| 2013/0142697 A1 | 6/2013 | Kim et al. | |
| 2013/0164763 A1 | 6/2013 | Saiki et al. | |
| 2013/0206701 A1 | 8/2013 | Strohmeier et al. | |
| 2013/0260481 A1 | 10/2013 | Shimizu et al. | |
| 2013/0261010 A1 | 10/2013 | Bailey et al. | |
| 2013/0266956 A1 | 10/2013 | Tia et al. | |
| 2013/0288351 A1 | 10/2013 | Nitta | |
| 2014/0004505 A1 | 1/2014 | Su et al. | |
| 2014/0073041 A1 | 3/2014 | Kijima | |
| 2014/0234184 A1 | 8/2014 | Oshika et al. | |
| 2014/0242721 A1 | 8/2014 | Kellogg et al. | |
| 2014/0270459 A1* | 9/2014 | Moll | G01N 33/56972 382/134 |
| 2014/0273192 A1* | 9/2014 | Sharpe | B01L 3/502761 435/288.7 |
| 2015/0087544 A1 | 3/2015 | Putnam et al. | |
| 2015/0093771 A1 | 4/2015 | Griss et al. | |
| 2015/0098864 A1 | 4/2015 | Yang | |
| 2015/0111778 A1 | 4/2015 | McDevitt et al. | |
| 2015/0251183 A1 | 9/2015 | Saiki | |
| 2015/0355132 A1 | 12/2015 | Crooks et al. | |
| 2017/0131304 A1 | 5/2017 | Johno et al. | |
| 2017/0138972 A1 | 5/2017 | Johno et al. | |
| 2017/0168046 A1 | 6/2017 | Saiki et al. | |
| 2017/0350910 A1 | 12/2017 | Okamoto et al. | |

FOREIGN PATENT DOCUMENTS

| | | |
|---|---|---|
| EP | 0871539 A1 | 10/1998 |
| EP | 1105457 A1 | 6/2001 |
| EP | 2072134 A2 | 6/2009 |
| EP | 2133150 A1 | 12/2009 |
| EP | 2 175 278 A1 | 4/2010 |
| EP | 2253958 A1 | 11/2010 |
| EP | 2311565 A1 | 4/2011 |
| EP | 2402460 A1 | 1/2012 |
| EP | 2602025 A1 | 6/2013 |
| JP | S60-159651 A | 8/1985 |
| JP | S61-264263 A | 11/1986 |
| JP | H01-227061 A | 9/1989 |
| JP | H05-297001 A | 11/1993 |
| JP | H05-322894 A | 12/1993 |
| JP | H07-500910 A | 1/1995 |
| JP | H08-262024 A | 10/1996 |
| JP | H09-218201 A | 8/1997 |
| JP | H09-257796 A | 10/1997 |
| JP | H09-325148 A | 12/1997 |
| JP | H10-300752 A | 11/1998 |
| JP | 2001-502793 A | 2/2001 |
| JP | 2002-236131 A | 8/2002 |
| JP | 2003-043052 A | 2/2003 |
| JP | 2004-163104 A | 6/2004 |
| JP | 2005-010031 A | 1/2005 |
| JP | 2005-345160 A | 12/2005 |
| JP | 2006-010535 A | 1/2006 |
| JP | 2006-068384 A | 3/2006 |
| JP | 2006-112824 A | 4/2006 |
| JP | 2006-177850 A | 7/2006 |
| JP | 2006-258696 A | 9/2006 |
| JP | 2007-003361 A | 1/2007 |
| JP | 2007-003414 A | 1/2007 |
| JP | 2007-010341 A | 1/2007 |
| JP | 2007-024851 A | 2/2007 |
| JP | 2007-047031 A | 2/2007 |
| JP | 2007-064742 A | 3/2007 |
| JP | 2007-071557 A | 3/2007 |
| JP | 2007-071655 A | 3/2007 |
| JP | 2007-078676 A | 3/2007 |
| JP | 2007-101240 A | 4/2007 |
| JP | 2007-279069 A | 10/2007 |

(56) References Cited

FOREIGN PATENT DOCUMENTS

| | | |
|---|---|---|
| JP | 2007-285792 A | 11/2007 |
| JP | 2007-530938 A | 11/2007 |
| JP | 2007-315879 A | 12/2007 |
| JP | 2008-064701 A | 3/2008 |
| JP | 2008-064748 A | 3/2008 |
| JP | 2008-128906 A | 6/2008 |
| JP | 2008-134126 A | 6/2008 |
| JP | 2008-157708 A | 7/2008 |
| JP | 2008-164360 A | 7/2008 |
| JP | 2008-164434 A | 7/2008 |
| JP | 2008-216237 A | 9/2008 |
| JP | 2009-014529 A | 1/2009 |
| JP | 2009-031116 A | 2/2009 |
| JP | 2009-042104 A | 2/2009 |
| JP | 2009-109251 A | 5/2009 |
| JP | 2009-121860 A | 6/2009 |
| JP | 2009-128342 A | 6/2009 |
| JP | 2009-133831 A | 6/2009 |
| JP | 2009-139289 A | 6/2009 |
| JP | 2009-156717 A | 7/2009 |
| JP | 2009-156778 A | 7/2009 |
| JP | 2009-162701 A | 7/2009 |
| JP | 2009-180688 A | 8/2009 |
| JP | 2009-180697 A | 8/2009 |
| JP | 2009-186296 A | 8/2009 |
| JP | 2009-210564 A | 9/2009 |
| JP | 2009-287971 A | 12/2009 |
| JP | 2010-071644 A | 4/2010 |
| JP | 2010-122022 A | 6/2010 |
| JP | 2010-151447 A | 7/2010 |
| JP | 2010-210531 A | 9/2010 |
| JP | 2010-243373 A | 10/2010 |
| JP | 2010-286297 A | 12/2010 |
| JP | 2011-007778 A | 1/2011 |
| JP | 2011-069618 A | 4/2011 |
| JP | 2011-183589 A | 9/2011 |
| JP | 2011-196849 A | 10/2011 |
| JP | 2012-143204 A | 8/2012 |
| JP | 2012-159325 A | 8/2012 |
| JP | 2012-215515 A | 11/2012 |
| JP | 2012-229985 A | 11/2012 |
| JP | 2013-050435 A | 3/2013 |
| JP | 2013-079812 A | 5/2013 |
| JP | 2013-205305 A | 10/2013 |
| JP | 2014-032018 A | 2/2014 |
| JP | 2014-044077 A | 3/2014 |
| JP | 2014-048209 A | 3/2014 |
| JP | 2014-106207 A | 6/2014 |
| JP | 2014-190906 A | 10/2014 |
| JP | 2014-232023 A | 12/2014 |
| JP | 2015-121493 A | 7/2015 |
| JP | 2015-197338 A | 11/2015 |
| JP | 2015-223562 A | 12/2015 |
| WO | 90/013016 A1 | 11/1990 |
| WO | 90/015321 A2 | 12/1990 |
| WO | 92/016844 A1 | 10/1992 |
| WO | 93/08893 A1 | 5/1993 |
| WO | 96/026011 A1 | 8/1996 |
| WO | 98/13684 A1 | 4/1998 |
| WO | 1999/064836 A1 | 12/1999 |
| WO | 01/087485 A2 | 11/2001 |
| WO | 02/23163 A1 | 3/2002 |
| WO | 05/075997 A1 | 8/2005 |
| WO | 2007/005077 A1 | 1/2007 |
| WO | 2007/105584 A1 | 9/2007 |
| WO | 2007/116909 A1 | 10/2007 |
| WO | 07/122943 A1 | 11/2007 |
| WO | 2008/053743 A1 | 5/2008 |
| WO | 2008/139697 A1 | 11/2008 |
| WO | 2010/044598 A2 | 4/2010 |
| WO | 10/058303 A1 | 5/2010 |
| WO | 2010/077159 A1 | 7/2010 |
| WO | 2012/164552 A1 | 12/2012 |
| WO | 2014/017018 A1 | 1/2014 |

OTHER PUBLICATIONS

International Search Report issued in corresponding International Patent Application No. PCT/JP2015/068724, dated Sep. 1, 2015; with English translation.
International Search Report issued in corresponding International Patent Application No. PCT/JP2015/068723, dated Sep. 29, 2015; with English translation.
International Search Report issued in corresponding International Patent Application No. PCT/JP2015/068722, dated Sep. 29, 2015; with English translation.
Extended European Search Report dated Dec. 21, 2017, issued in European Patent Application No. 15814780.1.
Chinese Search Report issued in Chinese Patent Application No. 201580035558.6, dated Dec. 15, 2017; with partial English translation.
Non-Final Office Action issued in related U.S. Appl. No. 15/323,001, dated Jun. 3, 2019.
International Search Report issued in International Patent Application No. PCT/JP2015/084738, dated Mar. 15, 2016; with English translation.
Extended European Search Report issued in European Patent Application No. 15866519.0, dated Jun. 19, 2018.
Notice of Allowance issued in related U.S. Appl. No. 15/322,977, dated Sep. 11, 2019.
Notice of Allowance issued in related U.S. Appl. No. 15/322,910, dated Feb. 25, 2019.

* cited by examiner

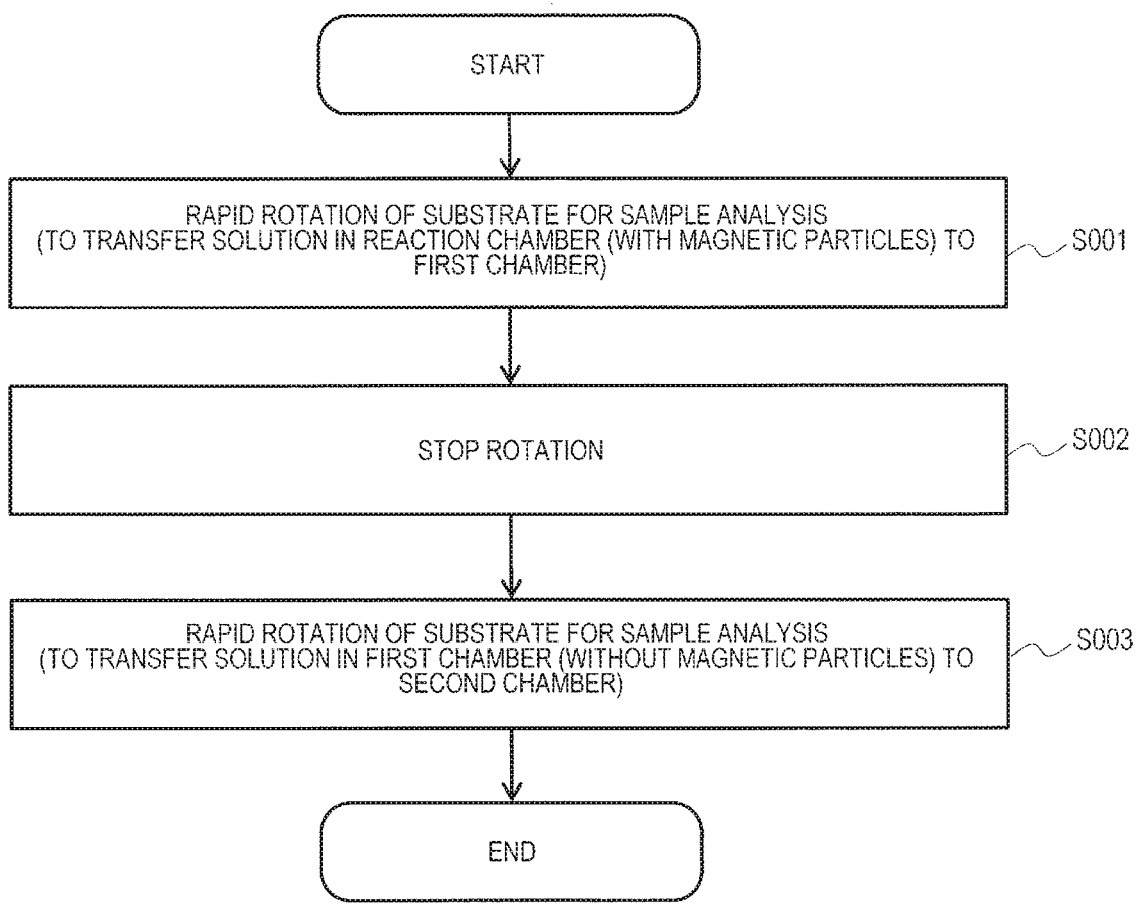

SUBSTRATE FOR SAMPLE ANALYSIS, SAMPLE ANALYSIS DEVICE, SAMPLE ANALYSIS SYSTEM, AND METHOD FOR REMOVING LIQUID FROM LIQUID THAT CONTAINS MAGNETIC PARTICLES

RELATED APPLICATIONS

This application is the U.S. National Phase under 35 U.S.C. § 371 of International Patent Application No. PCT/JP2015/068723, filed on Jun. 29, 2015, which in turn claims the benefit of Japanese Application No. 2014-134778, filed on Jun. 30, 2014, the disclosures of which Applications are incorporated by reference herein.

TECHNICAL FIELD

The present application relates to a substrate for sample analysis, a sample analysis device, a sample analysis system, and a method of removing the liquid from a liquid containing magnetic particles.

BACKGROUND ART

Techniques have been known which utilize a substrate for sample analysis in order to analyze a specific component within an analyte, such as urine or blood. For example, Patent Document 1 discloses a technique that utilizes a disk-shaped substrate for sample analysis, on which channels, chambers, and the like are formed. In this technique, the substrate for sample analysis is allowed to rotate, etc., thereby effecting transfer, distribution, mixing of solutions, analysis of components within an analyte solution, and so on.

CITATION LIST

Patent Literature

[Patent Document 1] Japanese National Phase PCT Laid-Open Publication No. 7-500910

SUMMARY OF INVENTION

Technical Problem

Analysis of specific components within an analyte includes assay techniques which utilize enzymatic reaction, immunoreaction, and the like, and involve complicated reaction steps. There has been a desire for a technique which allows assay techniques that involve such complicated reaction steps to be performed in a substrate for sample analysis.

A non-limiting, illustrative embodiment of the present application provides a substrate for sample analysis, a sample analysis device, a sample analysis system, and a method of removing the liquid from a liquid containing magnetic particles which support assay techniques that carry out analysis of components within an analyte through more complicated reaction steps.

Solution to Problem

A substrate for sample analysis according to one aspect of the present application is a substrate for sample analysis on which transfer of a liquid is to occur with rotational motion, comprising: a substrate having a rotation axis and a plate shape with a predetermined thickness; a first chamber being located in the substrate and having a first space for retaining a liquid and magnetic particles; a second chamber being located in the substrate and having a second space for retaining the liquid to be discharged from the first chamber; a channel being located in the substrate and having a path connecting the first chamber and the second chamber, the channel being capable of being filled via capillary action with the liquid retained in the first space; and a magnet being located in the substrate and near the first space in the substrate for capturing the magnetic particles in the first chamber.

The substrate may have at least one inner surface defining the first space in the substrate; the at least one inner surface may include a side face portion that is the farthest from the rotation axis; and the magnet may be located near the side face portion of the at least one surface and more distant from the rotation axis than is the side face portion; and the magnetic particles may be captured at the side face portion.

Advantageous Effects of Invention

A substrate for sample analysis, a sample analysis device, a sample analysis system, and a method of removing the liquid from a liquid containing magnetic particles according to one aspect of the present application support assay techniques that carry out analysis of components within an analyte through assay techniques that carry out analysis of components within an analyte through complicated reaction steps.

BRIEF DESCRIPTION OF DRAWINGS

FIG. 5 A flowchart showing an exemplary operation of the sample analysis system.

DESCRIPTION OF EMBODIMENTS

Assay techniques for components within an analyte such as urine or blood may utilize a combination reaction between the analyte being the subject for analysis and a ligand which specifically binds to the analyte. Examples of such assay techniques include immunoassay techniques and genetic diagnosis techniques.

Examples of immunoassay techniques are competitive assay and non-competitive assay (sandwich immunoassay). Examples of genetic diagnosis techniques are genetic detection techniques based on hybridization. In these immunoassay techniques and genetic detection techniques, magnetic particles (which may also be referred to as "magnetic beads", "magnetism particles", "magnetism beads", etc.) are used, for example. As an example of such assay techniques, a sandwich immunoassay utilizing magnetic particles will be specifically described.

Figure 1:
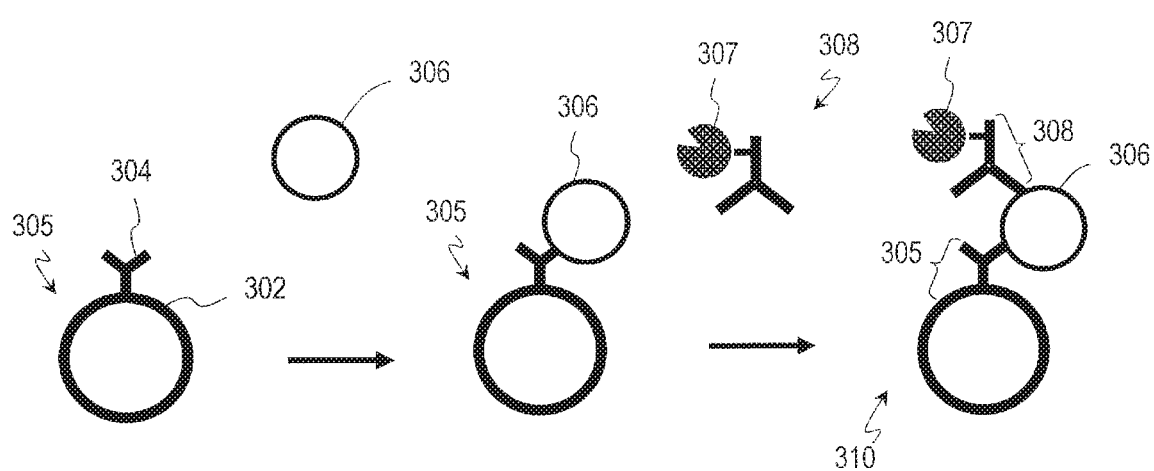
FIG. 1 An exemplary schematic diagram describing a sandwich immunoassay utilizing magnetic particles.

As shown in FIG. 1, first, a primary antibody 304 having a magnetic particle 302 immobilized to whose surface (hereinafter referred to as the "magnetic-particle-immobilized antibody 305") and an antigen 306, for which measurements are to be taken, are allowed to bind through an antigen-antibody reaction. Next, a secondary antibody to which a label substance 307 has bound (hereinafter referred to as a "labeled antibody 308") and the antigen 306 are allowed to bind through an antigen-antibody reaction. As a result, a composite 310 is obtained in which the magnetic-particle-immobilized antibody 305 and the labeled antibody 308 have bound to the antigen 306.

A signal which is based on the label substance 307 of the labeled antibody 308 that has bound to the composite 310 is detected, and an antigen concentration is measured in accordance with the amount of detected signal. Examples of the label substance 307 include enzymes (e.g., peroxidase, alkaline phosphatase, and luciferase), chemiluminescent substances, electrochemiluminescent substances, and fluorescent substances. In accordance with each such label substance 307, dye, luminescence, fluorescence, or other signals are detected.

In this series of reactions, in order to obtain the composite 310 as the reaction product, separation needs to be effected between unreacted substance in the analyte, substance that has non-specifically adsorbed to the magnetic particles or the like, and unreacted substance which was not involved in the formation of the composite 310 (e.g., the labeled antibody 308). This separation is called B/F separation (Bound/Free Separation). A B/F separation process is similarly required also in immunoassay techniques based on competitive assay and in genetic detection techniques based on hybridization. Examples of not using magnetic particles may include the use of: a ligand which is immobilized through physisorption to a solid phase composed of polystyrene, polycarbonate, or other materials, a ligand which is immobilized to a solid phase via a chemical bond, a ligand which is immobilized to the surface of a metal substrate composed of gold or the like (e.g., being immobilized by using a self-assembled monolayer (SAM)), and so on. In order to effect this B/F separation in the substrate for sample analysis, while surely capturing the magnetic particles in the solution (e.g., an analyte solution, a reaction solution, or a wash solution) with the magnetic force of a magnet, the solution needs to be removed.

Based on the technique disclosed in Patent Document 1, the inventors have specifically sought techniques which achieve B/F separation through rotation control of the substrate for sample analysis and designing of channels and chambers. As a result, they have arrived at a construction where, by using a substrate for sample analysis, the substrate including a first chamber as a place in which to effect B/F separation for a solution containing magnetic particles, a second chamber in which to accommodate the solution which has been removed from the first chamber, and a channel which is a capillary tube channel coupling the first chamber and the second chamber: magnetic particles in the first chamber are captured with a magnet while the substrate for sample analysis is rotated so that the resultant rotary force and the capillary action in the channel allow the solution to be discharged from the first chamber to the second chamber while the magnetic particles are retained in the first chamber. They have also arrived at a substrate for sample analysis which can achieve more reliable B/F separation with the aid of magnet positioning. In outline, a substrate for sample analysis, a sample analysis device, a sample analysis system, and a method of removing the liquid from a liquid containing magnetic particles according to one aspect of the present application are as follows.

[Item 1] A substrate for sample analysis on which transfer of a liquid is to occur with rotational motion, the substrate for sample analysis comprising:
a substrate having a rotation axis;
a substrate having a rotation axis;
a first chamber being located in the substrate and having a first space for retaining a liquid and magnetic particles;
a second chamber being located in the substrate and having a second space for retaining the liquid to be discharged from the first chamber;
a channel being located in the substrate and having a path connecting the first chamber and the second chamber; and
a magnet being located in the substrate and near the first space in the substrate for capturing the magnetic particles in the first chamber.

[Item 2] The substrate for sample analysis of item 1, wherein the channel is a capillary channel.

[Item 3] The substrate for sample analysis of item 1 or 2, wherein,
the substrate has at least one inner surface defining the first space in the substrate; and
the at least one inner surface includes a side face portion that is the farthest from the rotation axis, and the magnet is located near the side face portion of the at least one inner surface and more distant from the rotation axis than is the side face portion.

[Item 4] The substrate for sample analysis of any of items 1 to 3, wherein,
the substrate has a first principal face and a second principal face;
the at least one inner surface of the substrate includes an upper face portion and a lower face portion extending along the first principal face and the second principal face; and an opening of the channel in the first chamber is in contact with the lower face portion of the at least one inner surface.

[Item 5] The substrate for sample analysis of item 3, wherein the magnet is closer to the upper face portion than to the opening of the channel.

[Item 6] The substrate for sample analysis of any of items 3 to 5, wherein,
the substrate further has
a side face located between the first principal face and the second principal face, and
a receptacle having an opening in at least one of the first principal face, the second principal face, and the side face, the receptacle being located in the substrate; and
the magnet is accommodated in the receptacle.

[Item 7] The substrate for sample analysis of item 4, wherein,
as viewed from a direction which is perpendicular to the first principal face, the channel is connected to one end of the side face portion; where,
on the rotation axis side, a reference line is taken perpendicular to a line connecting an arbitrary reference point and the one end to which the channel is connected;
a plurality of points $a_1, a_2, a_3, \ldots a_h, a_{h+1} \ldots a_n$ are taken at an arbitrary interval from the one end to another end of the side face portion;
tangents as centered around the reference point are taken at the plurality of points $a_1, a_2, a_3, \ldots a_h, a_{h+1} \ldots a_n$; and
angles which are constituted by the reference line and the tangents at the plurality of points $a_1, a_2, a_3, \ldots a_h, a_{h+1} \ldots a_n$ are designated $\alpha_1, \alpha_2, \alpha_3, \ldots \alpha_h, \alpha_{h+1} \ldots \alpha_n$; then,
the relationship is $\alpha_1 \leq \alpha_2 \leq \alpha_3 \leq \ldots \leq \alpha_h < \alpha_{h+1} \leq \ldots \leq \alpha_n$ is satisfied; and
regardless of where the reference point is set, given distances $d_1, d_2, d_3, \ldots d_h, d_{h+1} \ldots d_n$ respectively between the reference point and the points $a_1, a_2, a_3, \ldots a_h, a_{h+1} \ldots a_n$, it never so happens that $d_1 = d_2 = d_3 = \ldots = d_h = d_{h+1} = \ldots = d_n$.

[Item 8] The substrate for sample analysis of item 4, wherein,
in a cross section which is parallel to a radial direction from the rotation axis and perpendicular to the first principal face, the channel is connected to one end of the side face portion; where,
a reference line is taken perpendicular to a line connecting an arbitrary reference point in the first space and the one end to which the channel is connected;
a plurality of points $a_1, a_2, a_3, \ldots a_h, a_{h+1} \ldots a_n$ are taken at an arbitrary interval from the one end to another end of the side face portion;
tangents as centered around the reference point are taken at the plurality of points $a_1, a_2, a_3, \ldots a_h, a_{h+1} \ldots a_n$; and
angles which are constituted by the reference line and the tangents at the plurality of points $a_1, a_2, a_3, \ldots a_h, a_{h+1} \ldots a_n$ are designated $a_1, a_2, a_3, \ldots a_h, a_{h+1} \ldots a_n$; then,
the relationship is $\alpha_1 \leq \alpha_2 \leq \alpha_3 \leq \ldots \leq \alpha_h < \alpha_{h+1} \leq \ldots \leq \alpha_n$ satisfied.

[Item 9] The substrate for sample analysis of any of items 1 to 5, wherein, in a cross section which is parallel to a radial direction from the rotation axis and perpendicular to the first principal face, the side face portion has a recess which is dented away from the rotation axis.

[Item 10] The substrate for sample analysis of any of items 1 to 5, wherein the side face portion includes a third side face subportion and a fourth side face subportion each extending along a direction which is perpendicular to a radial direction from the rotation axis, the third side face subportion and the fourth side face subportion being arranged along a thickness direction of the substrate, and the third side face subportion and the fourth side face subportion constituting a groove which is dented away from the rotation axis.

[Item 11] The substrate for sample analysis of any of items 1 to 10, wherein the magnet is configured so that, as viewed from a direction which is perpendicular to the first principal face, a magnetic flux density at both ends of the side face portion is smaller than a magnetic flux density in portions of the side face portion other than said both ends.

[Item 12] The substrate for sample analysis of item 11, wherein,
when the side face portion is split into two at an arbitrary position as viewing the side face portion from a direction which is perpendicular to the first principal face,
the magnet has an N pole in a portion thereof corresponding to one of the split portions and an S pole in a portion thereof corresponding to the other split portion.

[Item 13] The substrate for sample analysis of item 11, wherein, as viewed from a direction which is perpendicular to the first principal face, the magnet has a bow shape protruding toward the rotation axis and different magnetic poles respectively at the rotation axis side and an opposite side from the rotation axis.

[Item 14] The substrate for sample analysis of any of items 1 to 11, wherein, in the substrate, the second chamber is more distant form the rotation axis than is the first chamber.

[Item 15] The substrate for sample analysis of any of items 1 to 12, wherein the channel has a path connecting the first chamber and the second chamber by way of a position which is closer to the rotation axis than is the first chamber.

[Item 16] The substrate for sample analysis of item 15, wherein the channel has a bent structure which is convex toward the rotation axis, where, when a liquid exists in the first chamber, an apex portion of the bent structure is closer to the rotation axis than is the position of a liquid surface of the liquid.

[Item 17] A sample analysis system comprising:
the substrate for sample analysis of any of items 1 to 14; and
a sample analysis device including:
a motor to rotate the substrate for sample analysis around the rotation axis in a state where the rotation axis is at an angle which is not less than 0° and not more than 90° with respect to the direction of gravity,
a rotation angle detection circuit to detect a rotation angle of a shaft of the motor,
a drive circuit to control rotation of the motor and a rotation angle of the motor when stopped based on a result of detection by the rotation angle detection circuit, and
a control circuit including an arithmetic unit, a memory, and a program which is stored in the memory and executable by the arithmetic unit, to control based on the program an operation of the motor, the rotation angle detection circuit, the origin detection circuit, and the drive circuit,
wherein,
when the substrate for sample analysis with the first chamber being filled with a liquid containing magnetic particles is mounted to the sample analysis device,
(a) as the substrate for sample analysis is stopped at a predetermined rotation angle, the channel becomes filled with a portion of the liquid in the first chamber via capillary action,
(b) as the substrate for sample analysis is rotated at a rate causing a centrifugal force which is stronger than a capillary force acting on the liquid filling the channel, the liquid in the first chamber is moved through the channel to the second chamber while the magnetic particles are captured in the first chamber with the magnet.

[Item 18] A sample analysis device, suitable for a substrate for sample analysis which includes a substrate having a rotation axis and a plate shape with a predetermined thickness, a first chamber being located in the substrate and having a first space for retaining a liquid and magnetic particles, and a receptacle located in the substrate near the first space, wherein transfer of a liquid is to occur with rotational motion, the sample analysis device comprising:
a motor to rotate the substrate for sample analysis around the rotation axis in a state where the rotation axis is inclined at an angle which is not less than 0 degrees and not more than 90 degrees with respect to the direction of gravity;
a rotation angle detection circuit to detect an angle of a shaft of the motor;
a drive circuit to control rotation and a stopping angle of the motor based on a result of detection by the angle detector;
a magnet;
a driving mechanism to, while rotation by the motor is stopped, insert the magnet into the receptacle of the substrate for sample analysis and remove the magnet in the receptacle; and
a controller circuit to control an operation of the motor, the rotation angle detection circuit, the drive circuit, and the driving mechanism.

[Item 19] A sample analysis device, suitable for a substrate for sample analysis which includes a substrate having a rotation axis and a plate shape with a predetermined thickness, a first chamber being located in the substrate and having a first space for retaining a liquid and magnetic particles, and a receptacle being located in the substrate near the first space and having an opening in a principal face of the substrate, wherein transfer of a liquid is to occur with rotational motion, the sample analysis device comprising:
a turntable having a rotation axis, a bearing surface to support the substrate for sample analysis, and a magnet protruding from the bearing surface and being disposed at a position for insertion into the receptacle of the substrate for sample analysis supported on the bearing surface;
a motor to rotate the turntable around the rotation axis in a state where the rotation axis of the turntable is inclined at an angle which is not less than 0 degrees and not more than 90 degrees with respect to the direction of gravity;
an angle detector to detect an angle of a shaft of the motor;
a drive circuit to control rotation and a stopping angle of the motor based on a result of detection by the angle detector; and
a control circuit to control an operation of the motor, the angle detector, and the drive circuit.

[Item 20] A method of removing the liquid from a liquid containing magnetic particles, comprising:
providing a substrate for sample analysis, the substrate for sample analysis including a substrate having a rotation axis, a first chamber located in the substrate, a second chamber located in the substrate, and a channel being located in the substrate and having a path connecting the first chamber and the second chamber, the channel being a capillary channel, with a magnet being located near the first space in the substrate;
introducing a liquid containing magnetic particles into the first chamber of the substrate for sample analysis, and filling the channel with a portion of the liquid via capillary action; and,
by rotating the substrate for sample analysis around the rotation axis at a rate causing a centrifugal force which is stronger than a capillary force acting on the liquid filling the channel, transferring the liquid from the first chamber to the second chamber while capturing the magnetic particles in the first chamber.

[Item 21] The method of removing the liquid from a liquid containing magnetic particles of item 20, wherein, the first chamber has a first space;
the substrate has at least one inner surface defining the first space;
the at least one inner surface includes a side face portion that is the farthest from the rotation axis; and
the magnet is located near the side face portion of the at least one surface and more distant from the rotation axis than is the side face portion.

Figure 2A:
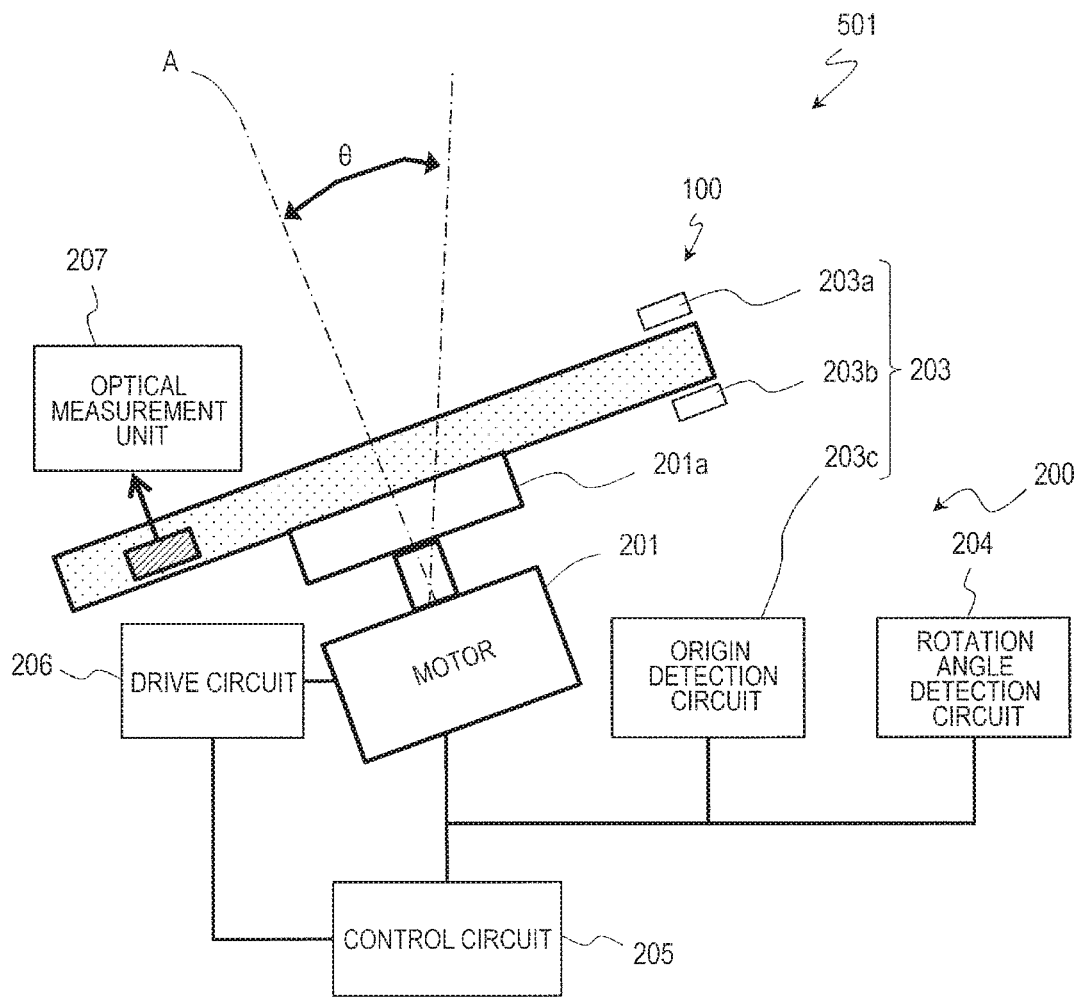
FIG. 2A A schematic diagram showing an exemplary construction of a sample analysis system according to an embodiment.

FIG. 2A is a schematic diagram showing an overall construction of the sample analysis system 501. The sample analysis system 501 includes a substrate 100 for sample analysis and a sample analysis device 200.

(Construction of the Sample Analysis Device 200)

The sample analysis device 200 includes a motor 201, an origin detector 203, a rotation angle detection circuit 204, a control circuit 205, a drive circuit 206, and an optical measurement unit 207.

The motor 201 includes a turntable 201*a* and a shaft A which is tilted from the direction of gravity at an angle θ which is not less than 0° and not more than 90° with respect to the direction of gravity, and rotates the substrate 100 for sample analysis placed on the turntable 201a around the shaft A. Since the shaft A is tilted by more than 0° but not more than 90°, not only a centrifugal force due to rotation but a gravity-based transfer can also be utilized for causing a transfer of any liquid in the substrate 100 for sample analysis. The angle of tilt of the shaft A with respect to the direction of gravity is preferably 5° or more, more preferably not less than 10° and not more than 45°, and still more preferably not less than 20° and not more than 30°. The motor 201 may be a DC motor, a brushless motor, an ultrasonic motor, or the like, for example.

Figure 2B:
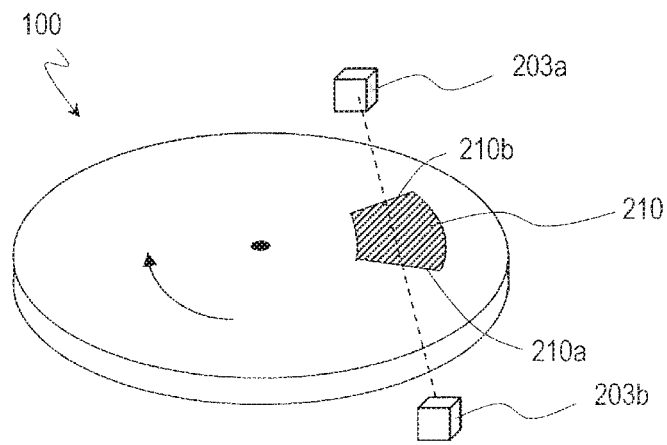
FIG. 2B A schematic diagram showing an exemplary construction for detecting an origin of a substrate for sample analysis in a sample analysis system.

The origin detector 203 detects an origin of the substrate 100 for sample analysis which is attached to the motor 201. For example, as shown in FIG. 2B, the origin detector 203 includes a light source 203a, a photodetector 203b, and an origin detection circuit 203c, and is disposed so that the substrate 100 for sample analysis comes between the light source 203a and the photodetector 203b. For example, the light source 203a may be a light-emitting diode, and the photodetector 203b may be a photodiode. The substrate 100 for sample analysis has a marker 210 at a specific position. The marker 210 has a light shielding ability to shade at least part of the light which exits the light source 203a, for example. The substrate 100 for sample analysis has a small transmittance (e.g. 10% or less) in the region of the marker 210, and a large transmittance (e.g. 60% or more) in the region other than the marker 210.

As the substrate 100 for sample analysis is rotated by the motor 201, the photodetector 203b outputs a detection signal which is in accordance with the amount of incident light on the origin detection circuit 203c. Depending on the direction of rotation, the detection signal may increase or decrease at an edge 210a and at an edge 210b of the marker 210. The origin detection circuit 203c detects a decrease in the amount of detected light and outputs it as an origin signal, for example, while the substrate 100 for sample analysis is rotating clockwise as indicated by the arrow. In the present specification, the position of the edge 210a of the marker 210 will be regarded as the origin position of the substrate 10 for sample analysis (i.e., a reference angular position of the substrate 100 for sample analysis). However, a position at any specific angle, as arbitrarily determined from the position of the edge 210a of the marker 210, might be defined as an origin. In the case where the marker 210 has a sector shape, with a central angle being smaller than the precision of angle detection that is required for sample analysis, the marker 210 itself may be regarded as the origin position.

The origin position is utilized by the sample analysis device 200 in acquiring information on the rotation angle of the substrate 100 for sample analysis. The origin detector 203 may have any other construction. For example, a magnet for use in origin detection may be provided on the substrate 100 for sample analysis, and, instead of the photodetector 203b, the origin detector 203 may include a magnetism detector which detects magnetism of this magnet. Moreover, a magnet for use in capturing the magnetic particles, as described later, may also be utilized for origin detection. In the case where the substrate 100 for sample analysis is attachable to the turntable 201a only at a specific rotation angle, the origin detector 203 may be omitted.

The rotation angle detection circuit 204 detects the rotation angle of the shaft A of the motor 201. For example, the rotation angle detection circuit 204 may be a rotary encoder that is attached to the shaft A. In the case where the motor 201 is a brushless motor, the rotation angle detection circuit 204 may include a Hall generator that is provided on the brushless motor and a detection circuit which receives an output signal from the Hall generator and outputs the angle of the shaft A.

The drive circuit 206 rotates the motor 201. Specifically, based on an instruction from the control circuit 205, the substrate 100 for sample analysis is rotated clockwise or counterclockwise. Moreover, based on results of detection by the rotation angle detection circuit 204 and the origin detector 203 and on an instruction from the control circuit 205, stops swings or rotation of the substrate 100 for sample analysis.

The optical measurement unit 207 detects a signal (e.g., dye, luminescence, fluorescence, etc.) which is in accordance with the label substance 307 of the labeled antibody 308 that has bound to the composite 310 (FIG. 1) being retained on the substrate 100 for sample analysis.

The control circuit 205 is a CPU which is provided in the sample analysis device 200, for example. By executing a computer program that is loaded into a RAM (Random Access Memory; not shown), the control circuit 205 sends instructions to other circuitry in accordance with the procedure defined by the computer program. Upon receiving such an instruction, each circuit operates as will be described in the present specification, whereby the function of the respective circuit is realized. The instructions from the control circuit 205 are sent to the drive circuit 206, the rotation angle detection circuit 204, the optical measurement unit 207, and the like, as shown in FIG. 2A, for example. The procedure defined by the computer program is shown by a flowchart in the attached drawings.

Note that a RAM into which a computer program is loaded, i.e., a RAM storing a computer program, may be volatile or non-volatile. A volatile RAM is a RAM which in the absence of supplied power is unable to retain the information that is stored therein. For example, a dynamic random access memory (DRAM) is a typical volatile RAM. A non-volatile RAM is a RAM which is able to retain information without power being supplied thereto. For example, a magnetoresistive RAM (MRAM), a resistive random access memory (ReRAM), and a ferroelectric memory (FeRAM) are examples of non-volatile RAMs. In the present embodiment, a non-volatile RAM is preferably adopted. A volatile RAM and a non-volatile RAM are both examples of non-transitory, computer-readable storage media. Moreover, a magnetic storage medium such as a hard disk, and an optical storage medium such as an optical disc are also examples of non-transitory, computer-readable storage media. That is, a computer program according to the present disclosure may be recorded on various non-transitory computer-readable media, excluding any medium such as the atmospheric air (transitory media) that allows a computer program to be propagated as a radiowave signal.

In the present specification, the control circuit 205 is described as a distinct component element from the rotation angle detection circuit 204 and the origin detection circuit 203c of the origin detector 203. However, these may be implemented by the same hardware. For example, in a serial or parallel manner, a CPU (computer) which is provided in the sample analysis device 200 may execute a computer program to function as the control circuit 205, a computer program to function as the rotation angle detection circuit 204, and a computer program to function as the origin detection circuit 203c of the origin detector 203. This allows the CPU to apparently operate as distinct component elements.

(Substrate 100 for Sample Analysis)

Figure 3A:
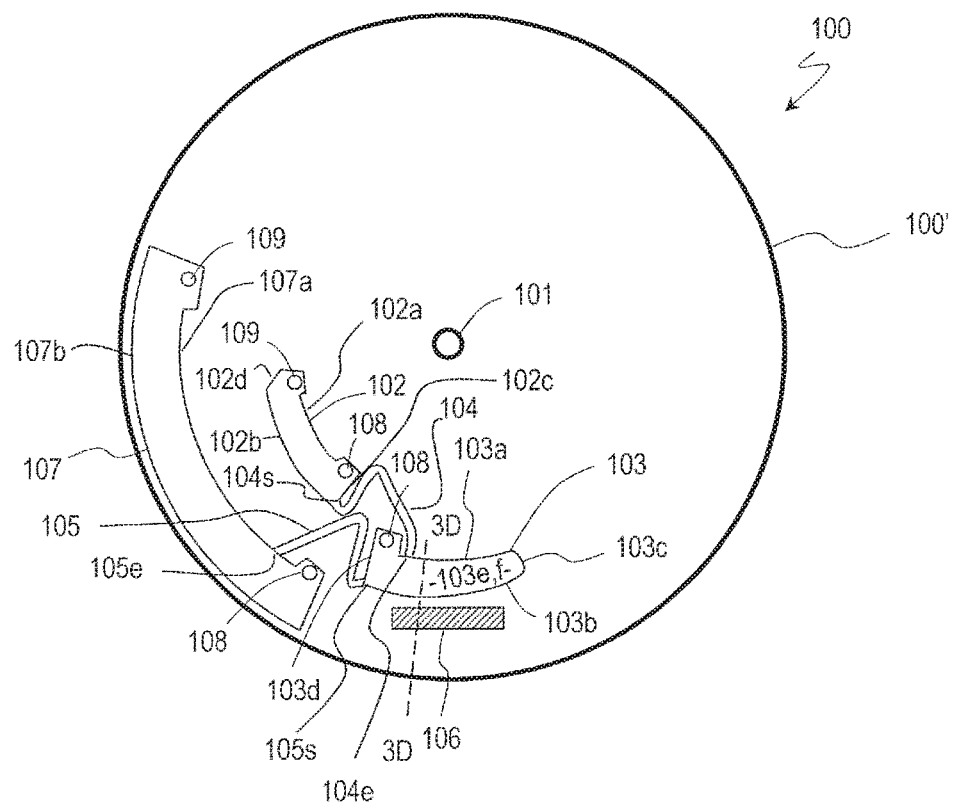
FIG. 3A A plan view of an exemplary structure of a substrate for sample analysis.
Figure 3B:
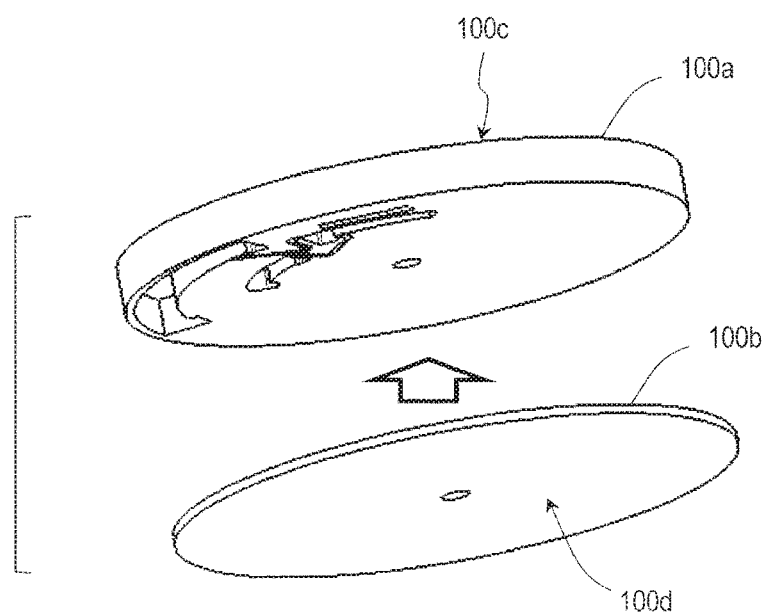
FIG. 3B An exemplary exploded perspective view of a substrate for sample analysis shown in FIG. 3A.

FIG. 3A and FIG. 3B are a plan view and an exploded perspective view of the substrate 100 for sample analysis. The substrate 100 for sample analysis includes a substrate 100' having a rotation axis 101 and a plate shape with a predetermined thickness along a direction which is parallel to the rotation axis. Although the substrate 100' of the substrate 100 for sample analysis has a circular shape in the present embodiment, it may alternatively be shaped as a polygon, an ellipse, a sector, or the like. The substrate 100' has two principal faces 100c and 100d. In the present embodiment, the principal face 100c and the principal face 100d are parallel to each other, and the thickness of the substrate 100' as defined by an interspace between the principal face 100c and the principal face 100d is constant irrespective of position within the substrate 100'. However, the principal faces 100c and 100d do not need to be parallel. For example, the two principal faces may be partly non-parallel or parallel, or be entirely non-parallel. Moreover, at least one of the principal faces 100c and 100d of the substrate 100' may have a structure with recesses or protrusions. The substrate 100 for sample analysis includes a reaction chamber 102, a first chamber 103, a second chamber 107, a channel 104 and a channel 105, located in the substrate 100'.

In the present embodiment, the substrate 100' of the substrate 100 for sample analysis is composed of a base substrate 100a and a cover substrate 100b. The respective spaces of the reaction chamber 102, the first chamber 103, and the second chamber 107 are formed within the base substrate 100a, and as the cover substrate 100b covers over the base substrate 100a, a top and a bottom of each space are created. In other words, the respective spaces of the reaction chamber 102, the first chamber 103, and the second chamber 107 are defined by at least one inner surface of the substrate 10 for sample analysis. The channel 104 and the channel 105 are also formed in the base substrate 100a, and as the cover substrate 100b covers over the base substrate 100a, a top and a bottom of the spaces of the channel 104 and the channel 105 are created. Thus, the reaction chamber 102, the first chamber 103, the second chamber 107, the channel 104, and the channel 105 are contained within the substrate 100'. In the present embodiment, the base substrate 100a and the cover substrate 100b are utilized respectively as an upper face and a lower face. The substrate 100' may be formed of a resin which may be acrylic, polycarbonate, polystyrene, or the like.

As has been described with reference to FIG. 1, the reaction chamber 102 is a reaction field in which the magnetic-particle-immobilized antibody 305, an analyte containing the antigen 306, and the labeled antibody 308 are allowed to react and form the composite 310. There is no particular limitation as to the shape of the reaction chamber 102. In the present embodiment, the substrate 100 for sample analysis includes the reaction chamber 102 as a reaction field where the composite 310 is allowed to form. Various means may be adopted in transferring the magnetic-particle-immobilized antibody 305, an analyte containing the antigen 306, and the labeled antibody 308 to the reaction chamber 102. For example, a mixed solution in which the magnetic-particle-immobilized antibody 305, the analyte containing the antigen 306, and the labeled antibody 308 have been previously mixed may be measured out, and the mixed solution may be injected into the reaction chamber 102 in the substrate 100 for sample analysis. Moreover, the substrate 100 for sample analysis may include chambers respectively retaining the magnetic-particle-immobilized antibody 305, the analyte containing the antigen 306, and the labeled antibody 308, and a channel (e.g., a capillary channel) via which each chamber and the reaction chamber 102 are coupled. In this case, the magnetic-particle-immobilized antibody 305, the analyte containing the antigen 306, and the labeled antibody 308 may be measured out into the respective chambers; the magnetic-particle-immobilized antibody 305, the analyte containing the antigen 306, and the labeled antibody 308 having been injected into the respective chambers may be transferred to the reaction chamber 102; and they may be mixed in the reaction chamber 102 to form the composite 310. Moreover, the magnetic-particle-immobilized antibody 305 and the labeled antibody 308 may be dried (hereinafter referred to as "dried reagents"). In this case, for example, the dried reagents may be retained in the reaction chamber 102, and dissolved by a liquid containing an analyte solution containing the antigen 306 to form the composite 310. Moreover, a dried reagent retained in a certain chamber during measurement may be dissolved by a predetermined solution, and an analyte solution containing the antigen 306 may be mixed in the reaction chamber 102, thereby allowing the composite 310 to form.

The space of the reaction chamber 102 is generally defined by side face portions 102a to 102d, and an upper face portion and a lower face portion, which are inner surfaces of the substrate 100'. The side face portions 103a and 103b are located along a radial direction from the rotation axis 101. The side face portion 103a is closer to the rotation axis 101 than is the side face portion 103b, and the side face portion 103b is more distant from the rotation axis 101 than is the side face portion 103a. Moreover, as can be seen from FIG. 3A, the side face portions 103c and 103d connect the side face portions 103a and 103b.

The channel 104 has a path connecting the reaction chamber 102 and the first chamber 103, as well as an end 104s and an end 104e. The end 104s is connected to the reaction chamber 102, and the end 104e is connected to the first chamber 103. The end 104s is closer to the rotation axis 101 than is the end 104e. With this construction, the solution containing the composite 310 receives a centrifugal force due to rotation of the substrate 100 for sample analysis, and is transferred to the first chamber 103 via the channel 104. Moreover, the end 104s is provided on, among side face portions of the reaction chamber 102, a side face portion 102b that is located at the outermost periphery side (i.e., away from the rotation axis 101). The reason is that, under a centrifugal force due to rotation of the substrate 100 for sample analysis, the solution containing the composite 310 will rest against the side face portion 102b. The end 104s may be provided at a side face portion 102c adjacent to the side face portion 102b, at a position near the side face portion 102b. In particular, it is preferable that the end 104s is provided at the side face portion 102c, at a position that encompasses the interconnection between the side face portion 102b and the side face portion 102c.

In the first chamber 103, B/F separation is to be effected for the solution containing the composite 310. For this purpose, the substrate 100 for sample analysis includes a magnet 106. In the substrate 100', the magnet 106 is located near the space of the first chamber 103.

More specifically, the space of the first chamber 103 is generally defined by the side face portions 103a to 103d, an upper face portion 103e, and a lower face portion 103f, which are inner surfaces of the substrate 100'. The side face portions 103a and 103b are located along a radial direction from the rotation axis 101. Moreover, as will be understood from FIG. 3A, the side face portions 103c and 103d are side faces connecting the side face portions 103a and 103b. The upper face portion 103e and the lower face portion 103f extend substantially along the two principal faces 100c and 100d of the plate shape of the substrate 100'. The side face portions 103a to 103d are located between the upper face portion 103e and the lower face portion 103f.

Preferably, the side face portion 102b which is the more distant from the rotation axis 101 between the two side face portions of the reaction chamber 102 is closer to the rotation axis 101 than is the side face portion 103b of the first chamber 103. More preferably, the side face portion 102b of the reaction chamber 102 is closer to the rotation axis 101 than is the side face portion 103a of the first chamber 103. With this construction, the solution containing the composite 310 within the reaction chamber 102 can entirely move to the first chamber 103, regardless of how much of it is retained.

As for the inner surfaces of the substrate 100' defining the space of the first chamber 103, the boundary between two adjacent side face portions, or the boundary between the side face portion and the upper face portion or lower face portion may not be parted by a clearly defined ridge. For example, the shape of the space of the first chamber 103 may be an oblate sphere or a spheroid. In this case, a pair of portions which are substantially perpendicular to a radial direction from the rotation axis 101 and a pair of portions which are parallel thereto are referred to as the side face portions, whereas a pair of portions which are substantially parallel to the two principal faces 100c and 100d of the plate shape of the substrate 100' are referred to as the upper face portion and the lower face portion. The same is also true of the reaction chamber 102 and the second chamber 107.

Figure 3C:
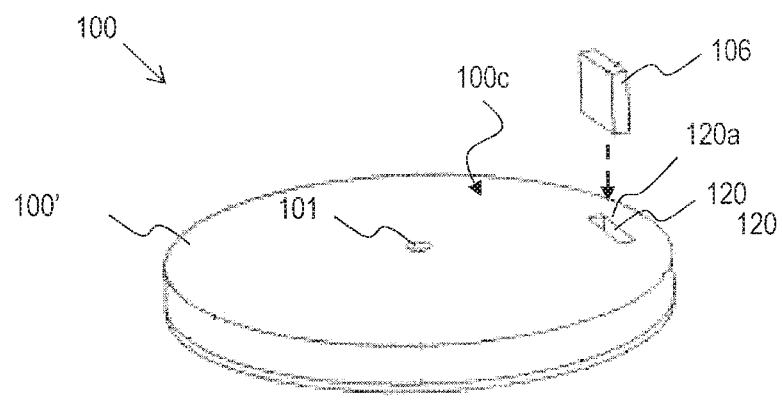
FIG. 3C A perspective view showing another exemplary structure of a substrate for sample analysis.

Among these inner surfaces, the magnet 106 is disposed near a side face portion that is the most distant from the rotation axis 101, the side face portion extending along the thickness direction of the substrate 100'. In the present embodiment, the magnet 106 is disposed near the side face portion 130b. The magnet 106 may be configured to be capable of being detachable in adaptation with B/F separation, or undetachably attached to the substrate 100 for sample analysis. In the case where the magnet 106 is configured to be detachable, for example, the substrate 100' has a receptacle in which the magnet 106 can be accommodated. For example, as shown in FIG. 3C, the substrate 100' may have a dented receptacle 120 with an opening 120a in the principal face 100c. The receptacle 120 has a space in which the magnet 106 can be accommodated. By inserting the magnet 106 through the opening 120a into the receptacle 120, the magnet 106 becomes mounted to the substrate 100'. The opening 120a of the receptacle 120 may be made in the principal face 100d, or in a side face that is located between the two principal faces 100c and 100d.

The magnet 106 is a magnet which is commonly used for immunoassay techniques based on competitive assay that utilize magnetism particles, for example. Specifically, ferrite magnet, neodymium magnets, and the like may be used. In particular, a neodymium magnet can be suitably used for the magnet 106 because of its strong magnetic force.

Figure 3D:
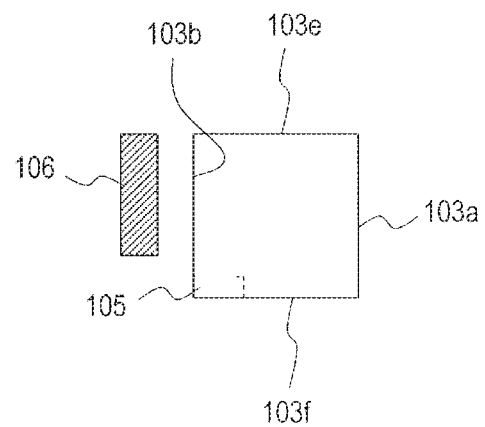
FIG. 3D A cross-sectional view taken along line 3D-3D in FIG. 3A.

FIG. 3D shows a cross section (broken line 3D-3D in FIG. A) containing the first chamber 103 and the magnet 106. As shown in FIG. 3D, the opening of the channel 105 at the first chamber 103 is in contact with the lower face portion 103f. Moreover, the magnet 106 is closer to the upper face portion 103e than to the opening of the channel 105.

As shown in FIG. 3A, the channel 105 has a path connecting the first chamber 103 and the second chamber 107, as well as an end 105s and an end 105e. The end 105s is connected to the first chamber 103, and the end 105e is connected to the second chamber 107. The end 105s is closer to the rotation axis 101 than is the end 105e. With this construction, under a centrifugal force due to rotation of the substrate 100 for sample analysis, the liquid which has been separated through B/F separation from the solution containing the composite 310 is transferred through the channel 105 to the second chamber 107.

Preferably, the end 105s is provided on, among side face portions of the first chamber 103, a side face portion 103b that is located at the outermost periphery side (i.e., away from the rotation axis 101). The reason is that the wash solution containing the composite 310 will rest against the side face portion 103b under a centrifugal force due to rotation of the substrate 100 for sample analysis. Alternatively, however, it may be provided at a side face portion 103d adjacent to the side face portion 103b, at a position near the side face portion 103b. It is particularly preferable that the end 105s is provided at the side face portion 103b and disposed at a position that encompasses the interconnection between the side face portion 103b and the side face portion 103d.

Preferably, the side face portion 103b of the first chamber 103 is closer to the rotation axis 101 than is the side face portion 107b which, between the two side face portions that define the space of the second chamber 107 and are located along a radial direction from the rotation axis 101, is the more distant from the rotation axis 101. More preferably, the side face portion 103b of the first chamber 103 is closer to the rotation axis 101 than is the side face portion 107a of the second chamber 107. With this construction, the solution in the first chamber 103 can entirely move to the second chamber 107.

The transfer of a liquid between the chambers by way of the channels can be attained by various methods. For example, a gravity-based transfer and a transfer based on a capillary force and a centrifugal force associated with rotation can be utilized. Hereinafter, these two transfer methods will be described in outline.

For example, the substrate 100 for sample analysis is supported so that its shaft A is tilted in a range which is greater than 0 degrees but not more than 90 degrees with respect to the vertical direction. Then, by changing the rotation angular position of the substrate 100 for sample analysis, the chamber from which the transfer occurs and in which a liquid exists is allowed to be disposed at a higher position than the chamber that is the destination of transfer. To be "high" means being located more upward along the vertical direction. As a result of this, the liquid can be transferred to the other chamber by utilizing gravity. In this case, the channel which couples between the chambers is not a capillary channel. A "capillary channel" would mean a channel with a narrow space which can be filled inside with a liquid via capillary action.

Moreover, a capillary channel may also be utilized in transferring a liquid to another chamber. A liquid transfer through a capillary channel will be described with respect to an exemplary construction including chamber A and chamber B, which are not capillary tube spaces, and a capillary channel, which connects between chamber A and chamber B. When a liquid being retained in chamber A comes in contact with an opening that defines an interconnection between chamber A and the capillary channel, the liquid is pulled into the capillary channel by a capillary force, whereby the interior of the channel becomes filled with the liquid. However, when the substrate 100 for sample analysis is rotated with such a number of revolutions (including also a stopped state) as will apply to the liquid inside the channel a centrifugal force which is equal to or less than the capillary force that is acting on the liquid inside the channel, then the liquid in the capillary channel will remain in the capillary tube space, without being transferred to chamber B. In order to fill the interior of the capillary channel with the liquid thus via capillary action, an air hole (air pathway between the external environment and the chamber) must be provided at the chamber B side, i.e., at the outlet side of the capillary channel. Moreover, in order to effect a liquid transfer via capillary action within the closed space defined by chamber A, chamber B, and the capillary channel, an air hole must also be provided at the chamber A side, i.e., at the inlet side of the capillary channel, as dictated by the relationship between air pressures inside the chambers and the channel.

Then, assuming that chamber B is disposed more distant from the rotation axis than is chamber A, from a state in which this capillary channel is filled with the liquid, the substrate 100 for sample analysis may be rotated with such a number of revolutions as will apply a centrifugal force which is greater than the capillary force that is acting on the liquid inside the capillary channel, whereby the liquid in chamber A can be transferred to chamber B with this centrifugal force.

In the case where a liquid is to be transferred with a capillary force or a centrifugal force due to rotation, for example, a substrate 100 for sample analysis having a diameter of 60 mm can be rotated in a range from 100 rpm to 8000 rpm. The rotation speed is determined in accordance with the shape of each chamber and channel, the physical properties of liquids, the timing of transfers of liquids and treatments, and the like.

The sizes of the spaces of the reaction chamber 102, the first chamber 103, and the second chamber 107 are e.g. about 10 µl to about 500 µl. Preferably, the channel 104 and the channel 105 are sized so that they can be filled with the liquids retained in the reaction chamber 102 and the first chamber 103 via capillary action. In other words, the channel 104 and the channel 105 are preferably capillary channels or capillary tubes. For example, the cross section of each of the channel 104 and the channel 105 which is perpendicular to the direction that they extend may have a width of 0.1 mm to 5 mm and a depth of 50 µm to 300 µm, or may have a width of 50µ or more (preferably 50 µm to 300 µm) and a depth of 0.1 mm to 5 mm.

In the case where the channel 104 and the channel 105 are capillary channels, a hydrophilic treatment may be performed for the inner surfaces of the substrate 100' defining the channel 104 and the channel 105, and the inner surfaces of the reaction chamber 102, the first chamber 103, and the second chamber 107 near their interconnections with the channel 104 and the channel 105. The hydrophilic treatment will large substantial capillary forces to act. The hydrophilic treatment can be performed by coating the aforementioned inner surfaces with a nonionic-type, cation-type, anion-type, or amphoteric-type surfactant, performing a corona discharge treatment, or providing minute physical ruggednesses, and so on, for example (see Japanese Laid-Open Patent Publication No. 2007-3361, for example).

At least one air hole 108 is provided in each of the reaction chamber 102, the first chamber 103, and the second chamber 107. As a result, the interior of each chamber is maintained at the environmental air pressure, so that the liquid can move the channels 104 and 105 by capillary action and the siphon principle. Moreover, an opening 109 through which to inject or discharge liquids such as an analyte solution, a reaction solution, or a wash solution may be made in the reaction chamber 102 and the second chamber 107. As used herein, the siphon principle means the liquid transfer being controlled based on a balance between the centrifugal force acting on the liquid due to rotation of the substrate 100 for sample analysis and a capillary force within the channel.

In the reaction chamber 102, the first chamber 103, and the second chamber 107, the air hole 108 and the opening 109 are preferably disposed on the upper face portion, toward the side face portion that is near the rotation axis 101. This restrains, even when the substrate 100 for sample analysis rotates with the reaction chamber 102, the first chamber 103, or the second chamber 107 being filled with a liquid, the air hole 108 and the opening 109 from coming in contact with the liquid to allow the liquid to move through the air hole 108 and the opening 109 to outside of the substrate 100 for sample analysis. The air hole 108 and the opening 109 may be provided on a side face portion of each chamber.

Moreover, the space of the reaction chamber 102, the first chamber 103, or the second chamber 107 preferably has a convex portion protruding toward the rotation axis 101, with the air hole 108 and opening 109 being located in this convex portion. Such construction will allow the air hole 108 and the opening 109 in the reaction chamber 102, the first chamber 103, or the second chamber 107 to be positioned as close to the rotation axis 101 along the radial direction as possible. Thus, the amount of liquid that can be retained in the reaction chamber 102, the first chamber 103, or the second chamber 107 without coming in contact with the air hole 108 and the opening 109 when the substrate 100 for sample analysis has rotated, within the chamber space, any dead space that is not available to retain a liquid can be reduced.

Figure 4:
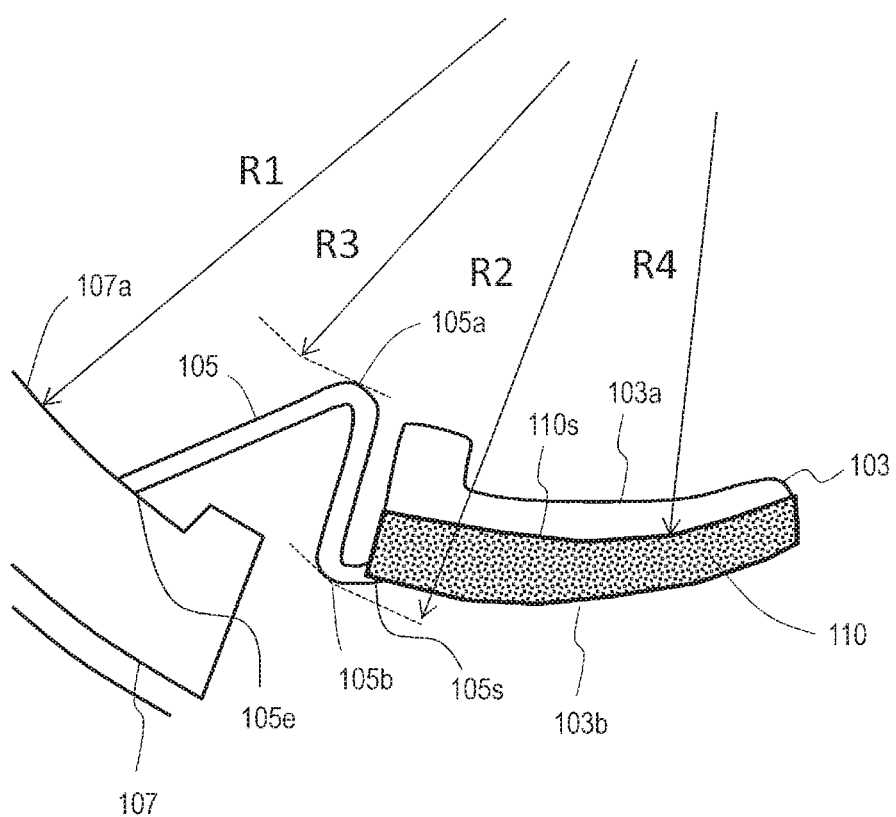
FIG. 4 A schematic diagram showing an exemplary positioning of a first chamber and a second chamber.

FIG. 4 shows positioning of the first chamber 103, the second chamber 107, and the channel 105. In the substrate 100 for sample analysis, the second chamber 107 is more distant from the rotation axis 101 than is the first chamber 103. As a result, the liquid retained in the first chamber 103 can be transferred to the second chamber 107 with a centrifugal force due to rotation of the substrate 100 for sample analysis. Moreover, use of a siphon structure and a capillary channel for the channel 105 connecting the first chamber 103 and the second chamber 107 allows for more strict control of transfer and stopping of liquids. As will be described in detail below, the siphon structure of the channel 105 allows the siphon principle to act on a centrifugal force due to rotation of the substrate 100 for sample analysis. Specifically, the channel 105 has two bent portions 105a and 105b. The bent portion 105b is located near the interconnection with the first chamber 103, and has a shape which is convex outward from the rotation axis 101.

The bent portion 105a is located between the bent portion 105b and the second chamber 107, and has a shape which is convex toward the rotation axis 101.

Given a distance R1 between the rotation axis 101 and the side face portion 107a, which is closest to the rotation axis 101, of the second chamber 107, and given a distance R2 from the rotation axis 101 to a point on the bent portion 105b that is farthest from the rotation axis 101, it is preferable that R1>R2 be satisfied.

Moreover, when a liquid 110 which is retained in the first chamber 103 concentrates toward the side face portion 103b due to centrifugal force, given a distance R4 from the rotation axis 101 to the liquid surface 110s of the liquid 110, and given a distance R3 from the rotation axis 101 to a point on the bent portion 105a that is nearest the rotation axis 101, it is preferable that R4>R3 be satisfied.

For example, consider a case where the substrate 100 for sample analysis is transferred from the reaction chamber 102 to the first chamber 103 through rotation, and rotation of the substrate 100 for sample analysis continues in this state, such that the centrifugal force due to this rotation involves a number of revolutions greater than the capillary force in the channel 105. In the case where it is not desired to transfer the liquid containing the composite 310 from the first chamber 103 to the second chamber 107, R4>R3 may be satisfied and the substrate 100 for sample analysis may be continuously rotated, whereby a centrifugal force acts on the liquid to prevent the liquid in the first chamber 103 from being transferred beyond the bent portion 105b of the channel 105 that has a high potential energy.

Moreover, in the case where a liquid is to be transferred from the first chamber 103 to the second chamber 107, rotation of the substrate 100 for sample analysis may be effected with such a number of revolutions (including also halted rotation) as will apply a centrifugal force which is equal to or less than the capillary force, whereby the channel 105 will become filled with the liquid via capillary action. Thereafter, the substrate 100 for sample analysis may be rotated with such a number of revolutions as will apply a centrifugal force which is stronger than the capillary force, this centrifugal force causing the liquid to be transferred to the second chamber 107. Thus, use of a capillary channel and a siphon structure for the channel 105 connecting the first chamber 103 and the second chamber 107 allows for more strict control of transfer and stopping of liquids. For example, in the case where the solution containing the composite 310 is to be transferred from the reaction chamber 102 to the first chamber 103 with a centrifugal force, the solution containing the composite 310, which has been transferred from the first chamber 103, can be prevented from being straightforwardly transferred to the second chamber 107.

On the other hand, in the case where the channel 105 is a capillary channel which lacks siphon structure, when transferring a liquid from the reaction chamber 102 to the second chamber 107 via the first chamber 103 based on a centrifugal force due to rotation of the substrate 100 for sample analysis, the liquid which has been transferred to the first chamber 103 will fill inside the channel 105 because of a capillary force in the channel 105. If rotation of the substrate 100 for sample analysis continues in this state, the liquid will not be retained in the first chamber 103, but will be transferred over to the second chamber 107 through the channel 105. The rotation of the substrate 100 for sample analysis as referred to herein is based on a number of revolutions that allows a centrifugal force which is stronger than the capillary force in the channel 105.

Thus, in the case where the liquid is to be transferred from the reaction chamber 102 to the first chamber 103 with the aforementioned number of revolutions, and the liquid is to be once retained in the first chamber 103 without allowing the liquid to be straightforwardly transferred to the second chamber 107, it is preferable that the channel 105 be based on a siphon structure.

In the present embodiment, as shown in FIG. 3A, the channel 104 also has a siphon structure. However, the channel 104 does not need to have a siphon structure. Moreover, a siphon structure may also be adopted even in the case where the aforementioned liquid control is not needed.

Although the present embodiment illustrates an example where the channel 105 is a capillary channel with a siphon structure as described above, the channel 104 and the channel 105 may be capillary channels lacking siphon structure, or channels utilizing gravity.

In the course of transferring a liquid from the reaction chamber 102 to the second chamber 107 via the first chamber 103, if the liquid is to be once retained in the first chamber 103, given a channel 105 which is a capillary channel lacking siphon structure, the following construction will be preferable. First, transfer of a liquid from the reaction chamber 102 to the first chamber 103 needs to be performed with such a number of revolutions (including also a stopped state) of the substrate 100 for sample analysis as will apply a centrifugal force which is equal to or less than a capillary force acting on the liquid filling the channel 105. In this case, the channel 104 is preferably a channel utilizing gravity. Moreover, inasmuch as the channel 104 is a channel utilizing gravity, the side face portion 102b of the reaction chamber 102 (shown in FIG. 3A) is preferably formed so that the side face portion 102b presents a dented shape allowing a liquid to be retained with the side face portion 102b while the substrate 100 for sample analysis is retained at a predetermined angle. In this case, transfer of the liquid from the reaction chamber 102 to the first chamber 103 is effected by changing the rotation angle of the substrate 100 for sample analysis so that the liquid which is retained in the recess of the side face portion 107b will move through the third channel 112 based on gravity.

On the other hand, in the course of transferring a liquid from the reaction chamber 102 to the second chamber 107 via the first chamber 103, if the liquid is to be once retained in the first chamber 103, given a channel 105 which is a channel utilizing gravity, the following construction will be preferable. The channel 104 may be either a capillary channel (including a siphon structure) or a channel utilizing gravity; however, the side face portion 103b of the first chamber 103 (shown in FIG. 3A) is preferably formed so that the side face portion 103b presents a dented shape allowing a liquid to be retained with the side face portion 103b while the substrate 100 for sample analysis is retained at a predetermined angle. In this case, transfer of the liquid from the first chamber 103 to the second chamber 107 is effected by changing the rotation angle of the substrate 100 for sample analysis so that the liquid retained in the recess of the side face portion 107b moves through the third channel 112 based on gravity.

As described above, the construction of the channel 104 and the channel 105 may be of various types.

(Operation of the Sample Analysis System 501)

Figure 6A:
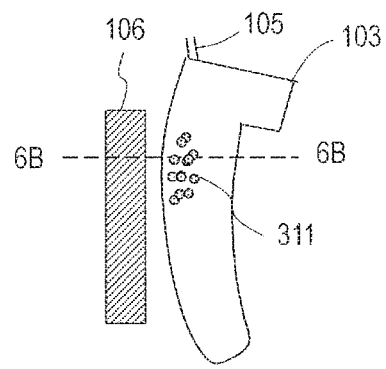
FIG. 6A A schematic diagram showing an exemplary distribution of composite within the first chamber during a sample analysis system operation.
Figure 6B:
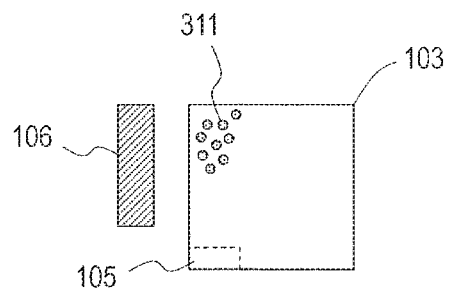
FIG. 6B A cross-sectional view taken along line 6B-6B in FIG. 6A.
Figure 6C:
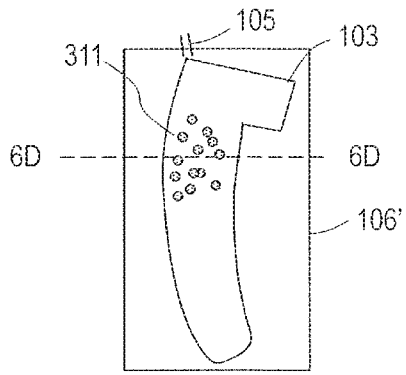
FIG. 6C A schematic diagram showing an exemplary distribution of composite within the first chamber in the case where the magnet is at a lower face of the first chamber.
Figure 6D:
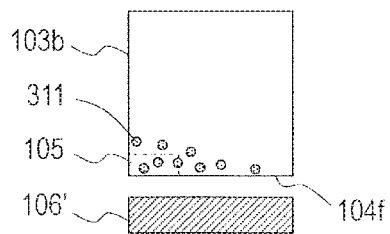
FIG. 6D A cross-sectional view taken along line 6D-6D in FIG. 6C.

With reference to FIG. 1, FIG. 3A, FIG. 5, and FIG. 6A to FIG. 6D, an operation of the sample analysis system 501 will be described. FIG. 5 is a flowchart showing an operation of the sample analysis system 501. FIG. 6A and FIG. 6C are plan views showing a distribution of composite 310 in the first chamber 103, whereas FIG. 6B and FIG. 6D are cross-sectional views taken along line 6B-6B and line 6D-6D in FIG. 6A and FIG. 6C.

First, in the reaction chamber 102, the magnetic-particle-immobilized antibody 305, the analyte containing the antigen 306, and the labeled antibody 308 are allowed to simultaneously react, thus forming the composite 310. For example, the reaction chamber 102 may retain a liquid containing the magnetic-particle-immobilized antibody 305, while chambers (not shown) that are provided in the substrate 100 for sample analysis may separately retain respective liquids containing the antigen 306 and the labeled antibody 308, and these may be transferred to the reaction chamber 102 with a centrifugal force due to rotation of the substrate 100 for sample analysis.

After the composite 310 is generated through the antigen-antibody reaction, as shown at step S001 first, the substrate 100 for sample analysis is rotated, thus moving the solution containing the composite 310 and the unreacted magnetic-particle-immobilized antibody 305 to the first chamber 103. At this point, while the substrate 100 for sample analysis is stopped, the channel 104 is filled with the liquid in the reaction chamber 102 due to capillary action. Therefore, as the rotation applies a centrifugal force which is stronger than the capillary force acting on the reaction liquid in the channel 104 to the solution containing the composite 310 in the reaction chamber 102, the solution containing the composite 310 is transferred to the first chamber 103. While the substrate 100 for sample analysis is rotating, the solution containing the composite 310 that has been transferred to the first chamber 103 will not be transferred further to the second chamber 107. The reason is that, as described earlier, the channel 105 constitutes a siphon; this prevents the liquid from moving through the channel 105 in a direction toward the rotation axis 101 against the centrifugal force.

The rotation speed of the substrate 100 for sample analysis is set to a rate such that a centrifugal force occurring through rotation ensures that the reaction liquid and other liquids will not be moved based on gravity and that a centrifugal force which is stronger than the capillary force in each capillary channel will be applied. Hereinafter, for any rotation utilizing a centrifugal force, this rotation speed will be set.

After the solution containing the composite 310 is entirely transferred to the first chamber 103, as shown at step S002, the substrate 100 for sample analysis is stopped at a predetermined rotation angle.

When the liquid containing the composite 310 and the unreacted magnetic-particle-immobilized antibody 305 is transferred from the reaction chamber 102 to the first chamber 103, the composite 310 and the unreacted magnetic-particle-immobilized antibody 305 (hereinafter, any allusion to both of these simultaneously will be made simply as the magnetic particles 311) are drawn toward the side face portion 103b by the magnetic force of the magnet 106.

In a state where rotation of the substrate 100 for sample analysis is stopped, the channel 105 is filled with the liquid in the first chamber 103 via capillary action.

As shown at step S003, when the substrate 100 for sample analysis is rotated, a centrifugal force occurs with the rotation, and acts on the liquid and the magnetic particles containing the composite 310 in the first chamber 103. The direction in which this centrifugal force acts is identical to the direction of the attractive force that the magnetic particles 311 receive from the magnet 106. Therefore, the magnetic particles 311 are strongly pressed against the side face portion 103b.

Under the centrifugal force, the liquid is discharged from the channel 105, and transferred to the second chamber 107.

At this time, the magnetic particles 311 receive a force from the moving liquid, and attempt to move to the channel 105 together with the liquid. However, as mentioned earlier, with a sum of the centrifugal force and the attractive force of the magnet, the magnetic particles 311 are strongly pressed against the side face portion 103b. As a result, only the liquid is discharged from the channel 105, while the magnetic particles 311 remain in the first chamber 103. Moreover, as shown in FIG. 6B, the magnet 106 is disposed above the opening of the channel 105, thereby making it difficult for the magnetic particles 311 to gather near the opening of the channel 105. Therefore, also in terms of where the magnetic particles 311 remain, the magnetic particles 311 are less likely to flow out from the channel 105.

After the liquid has all moved to the second chamber 107, rotation of the substrate 100 for sample analysis is stopped. This completes B/F separation, whereby the liquid and the magnetic particles 311 in the first chamber 103 become separated. Specifically, the liquid moves from the first chamber 103 to the second chamber 107, whereas the magnetic particles 311 remain in the first chamber 103. As shown in FIG. 6A, even after the substrate 100 for sample analysis stops rotating, the attractive force received from the magnet 106 allows the magnetic particles 311 to keep gathered at the side face portion 103b.

Thereafter, the optical measurement unit 207 is used to detect dye, luminescence, fluorescence, or other signals which are in accordance with the label substance 307 of the labeled antibody 308 having been bound to the composite 310 contained in the magnetic particles 311. Thus, it is possible to achieve detection of the antigen 306, quantification of the concentration of the antigen 306, and so on. Moreover, since the composite 310 has gathered at the side face portion 103b as described above, luminescence intensity or the like can be detected efficiently, thereby making it possible to enhance sensitivity of detection.

FIG. 6C is a plan view schematically showing a distribution of magnetic particles 311 when the magnet 106 is disposed at the lower face portion 103f of the first chamber 103 and the substrate 100 for sample analysis is rotated, and FIG. 6D is a cross-sectional view taken along line 6D-6D in FIG. 6C. In the case where the magnet 106' is disposed at the lower face portion 103f of the first chamber 103, the magnetic particles 311 are drawn toward the lower face portion 103f. On the other hand, centrifugal force acts to move the magnetic particles 311 toward the side face portion 103b. Therefore, the two forces are orthogonal, from which no large resultant force is obtained. As a result, the force of capturing the magnetic particles 311 is weaker than in the case where the magnet is near the side face portion 103b.

Moreover, the magnetic particles 311 are gathered near the boundary between the side face portion 103b and the lower face portion 103f. Since the opening of the channel 105 exists at this position, with movement of the solution, the composite 310 also becomes likely to flow out to the channel 105.

Thus, with the substrate for sample analysis, sample analysis device, and sample analysis system according to the present embodiment, by using a substrate for sample analysis, the substrate including a first chamber as a place in which to effect B/F separation for a solution containing magnetic particles, a second chamber in which to accommodate the solution which has been removed from the first chamber, and a channel which is a capillary tube channel coupling the first chamber and the second chamber, magnetic particles in the first chamber are captured with a magnet while the substrate for sample analysis is rotated so that the resultant rotary force and the capillary action in the channel allow the solution to be discharged from the first chamber to the second chamber while the magnetic particles are retained in the first chamber. This enables more complicated control of transfer, distribution, and mixing of analyte-containing solutions and reagents, and so on. Moreover, by placing the magnet near a side face portion of the first chamber that is the farthest from the rotation axis, a more reliable B/F separation can be effected. Furthermore, the composite possesses a high distribution density after B/F separation, and thus the label substance in the composite can be detected with a high sensitivity through spectroscopic analysis.

(Variants of the Side Face Portion 103b of the First Chamber 103)

Hereinafter, variants of the side face portion 103b of the first chamber 103 will be described.

Figure 7A:
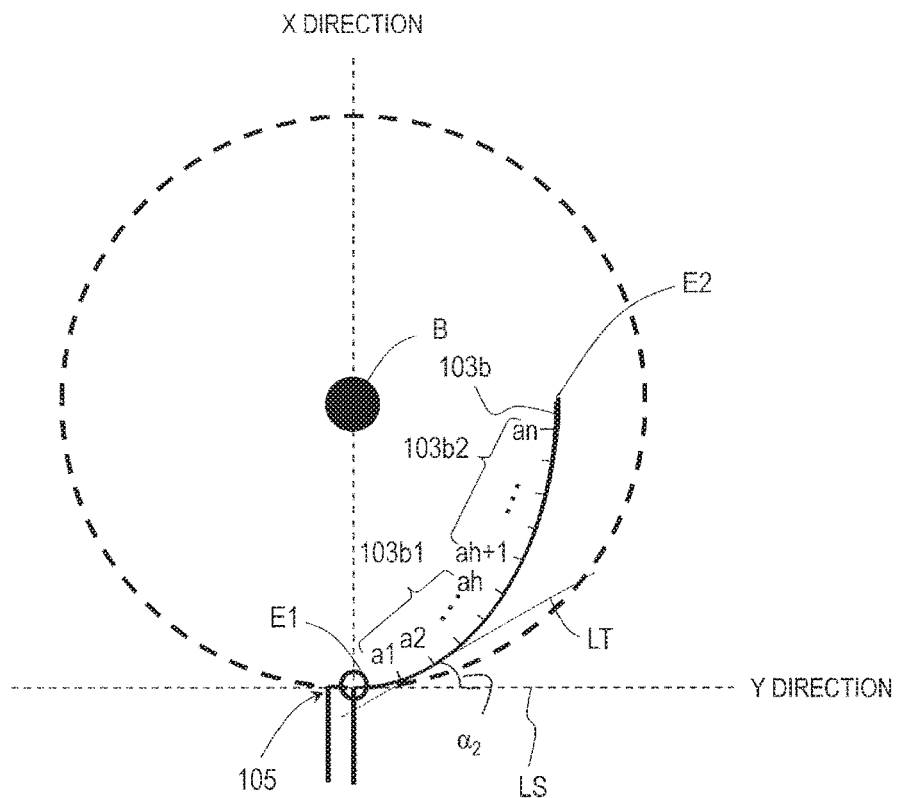
FIG. 7A A diagram explaining an exemplary shape of a side face portion of the first chamber as viewed from a direction which is perpendicular to a principal face.
Figure 7B:
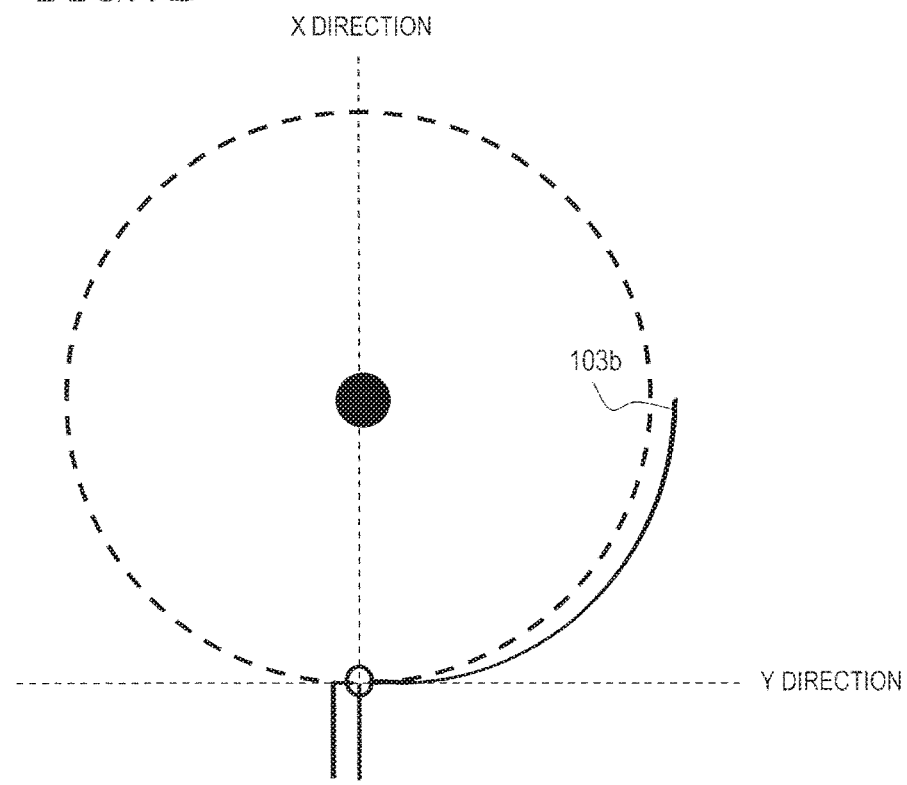
FIG. 7B A diagram explaining another exemplary shape of a side face portion of the first chamber as viewed from a direction which is perpendicular to a principal face.

FIG. 7A and FIG. 7B generally show the shape of the side face portion 103b of the first chamber 103 as viewed from a direction which is parallel to the rotation axis 101, i.e., perpendicular to a principal face 100m of the substrate 100 for sample analysis. The channel 105 is connected to one end E1 of the side face portion 103b. In this case, an arbitrary reference point B is taken on the rotation axis 101 side on the substrate 100 for sample analysis, and a reference line LS is taken perpendicular to a straight line connecting the reference point B and the one end E1 of the side face portion 103b to which the channel 105 is connected. From the one end E1 to the other end E2 of the side face portion 103b, a plurality of points $a_1, a_2, a_3, \ldots a_h, a_{h+1} \ldots a_n$ are taken at an arbitrary interval. Moreover, a tangent LT as centered around the reference point B is taken at each point $a_1, a_2, a_3, \ldots a_h, a_{h+1} \ldots a_n$; and the angles which are constituted by the reference line LS and the tangents LT at the points $a_1, a_2, a_3, \ldots a_h, a_{h+1} \ldots a_n$ are designated $\alpha_1, \alpha_2, \alpha_3, \ldots \alpha_h, \alpha_{h+1} \ldots \alpha_n$. The portion in which the points $a_1, a_2, a_3, \ldots a_h$ are located is designated the first side face subportion 103b1, whereas the portion in which the points $\alpha_{h+1} \ldots \alpha_n$ an are located is designated the second side face subportion 103b2.

In this case, the angles $\alpha_1, \alpha_2, \alpha_3, \ldots \alpha_h, \alpha_{h+1} \ldots \alpha_n$ satisfy the following relational expression (1).

$$\alpha_1 \leq \alpha_2 \leq \alpha_3 \leq \ldots \leq \alpha_h < \alpha_{h+1} \leq \ldots \leq \alpha_n \tag{1}$$

However, regardless of where the reference point B is set, given the distances $d_1, d_2, d_3, \ldots d_h, d_{h+1} \ldots d_n$ between the reference point B and the points $\alpha_1, \alpha_2, \alpha_3, \ldots \alpha_h, \alpha_{h+1} \ldots \alpha_n$, it never so happens that $d_1, d_2, d_3, \ldots d_h, d_{h+1} \ldots d_n$.

FIG. 7A and FIG. 7B show shapes of the side face portion 103b in the case where the amount of change among $\alpha_1, \alpha_2, \alpha_3, \ldots \alpha_h, \alpha_{h+1} \ldots \alpha_n$ is large and in the case where it is small. By providing the side face portion 103b with any such shape, the centrifugal force acting on the solution containing the magnetic particles 311 will make it easier for the solution to be discharged from the channel 105 at the end E1, easier for the magnetic particles 311 to gather more toward the center than the end E1 of the side face portion 103b, and restrain the magnetic particles 311 from being discharged at the channel 105.

Figure 8:
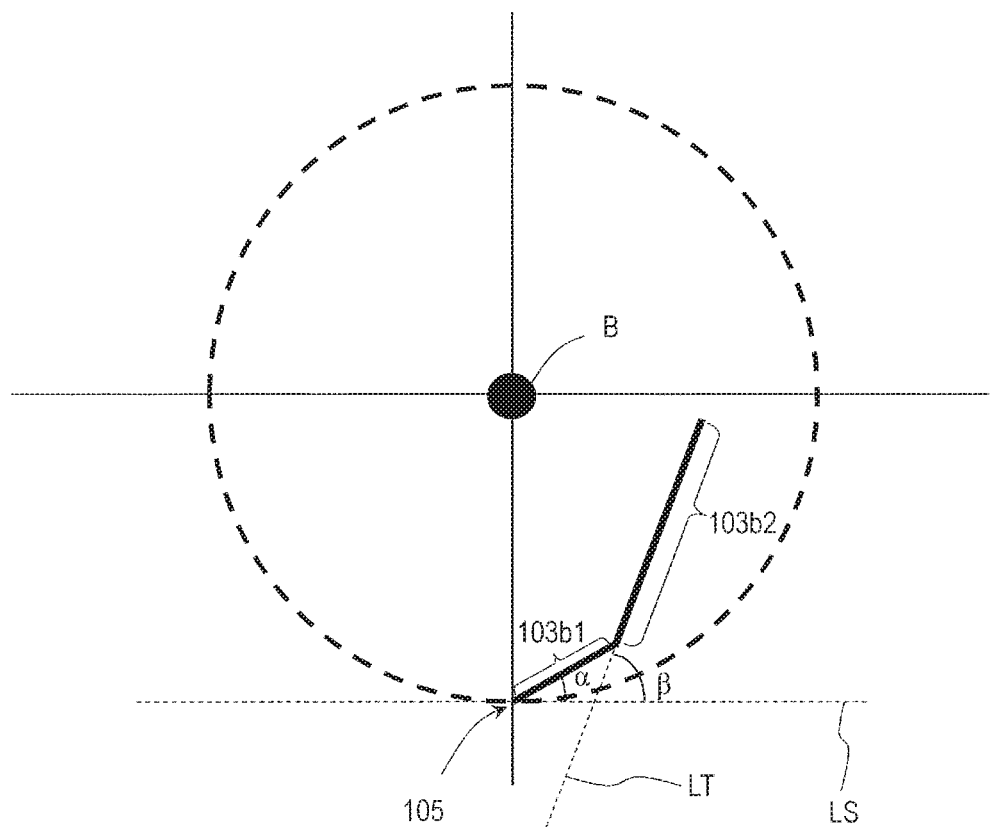
FIG. 8 A diagram explaining another exemplary shape of a side face portion of the first chamber.

In expression (1), when $\alpha_1 = \alpha_2 = \alpha_3 = \ldots = \alpha_h = \alpha_{h+1} = \ldots = \alpha_n$, as shown in FIG. 8, the side face portion 103b includes a first side face subportion 103b1 that constitutes an angle of $\alpha_1 = \alpha_2 = \alpha_3 = \ldots = \alpha_h$ with respect to the reference line LS and a second side face subportion 103b2 that constitutes an angle of $\alpha_{h+1} = \ldots = \alpha_n$ with respect to the reference line LS.

Figure 9:
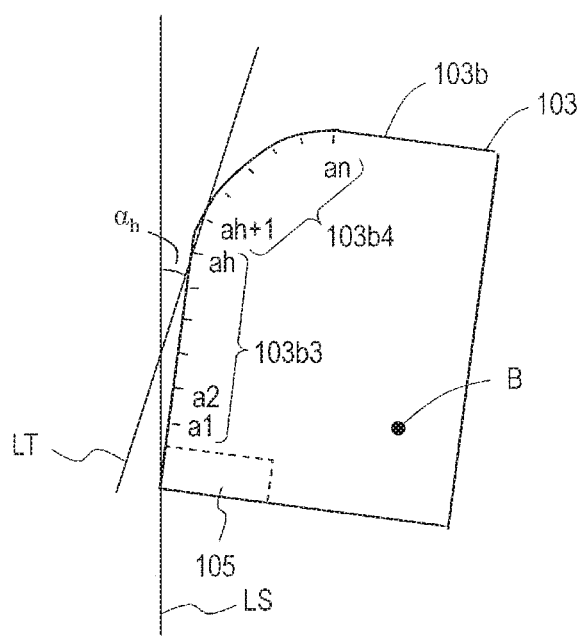
FIG. 9 A diagram explaining an exemplary shape of a side face portion of the first chamber, in a cross section taken parallel to the radial direction.

The shape of the side face portion 103b in a cross section which is parallel to a radial direction from the rotation axis 101 and is perpendicular to the principal face 100m can also be similarly constructed. FIG. 9 generally shows a shape of the side face portion 103b in a cross section which is parallel to a radial direction from the rotation axis 101 and is perpendicular to the principal face 100m. The channel 105 is connected to one end E1 of the side face portion 103b. In this case, an arbitrary reference point B is taken in the space of the first chamber 103, and a reference line LS is taken perpendicular to a straight line connecting the reference point B and the one end E1 of the side face portion 103b to which the channel 105 is connected. From the one end E1 to the other end E2 of the side face portion 103b, a plurality of points $a_1, a_2, a_3, \ldots a_h, a_{h+1} \ldots a_n$ are taken at an arbitrary interval.

Moreover, a tangent LT as centered around the reference point B is taken at each point $a_1, a_2, a_3, \ldots a_h, a_{h+1} \ldots a_n$; and the angles which are constituted by the reference line LS and the tangents LT at the points $a_1, a_2, a_3, \ldots a_h, a_{h+1} \ldots a_n$ are designated $\alpha_1, \alpha_2, \alpha_3, \ldots \alpha_h, \alpha_{h+1} \ldots \alpha_n$. The portion in which the points $a_1, a_2, a_3, \ldots a_h$ are located is designated the third side face subportion 103b3, whereas the portion in which the points $\alpha_h \ldots \alpha_n$ are located, is designated the fourth side face subportion 103b4.

In this case, the angles $\alpha_1, \alpha_2, \alpha_3, \ldots \alpha_h, \alpha_{h+1} \ldots \alpha_n$ satisfy the following relational expression (1).

$$\alpha_1 \leq \alpha_2 \leq \alpha_3 \leq \ldots \leq \alpha_h < \alpha_{h+1} \leq \ldots \leq \alpha_n \tag{1}$$

By providing the side face portion 103b with such a shape, in a cross section which is parallel to a radial direction from the rotation axis 101 and is perpendicular to the principal face 100m, too, the side face portion 103b will allow the centrifugal force acting on the solution containing the magnetic particles 311 to make it easier for the solution to be discharged from the channel 105 at the end E1, easier for the magnetic particles 311 to gather more toward the upper face portion than the end E1 of the side face portion 103b, and restrain the magnetic particles 311 from being discharged at the channel 105.

Figure 10A:
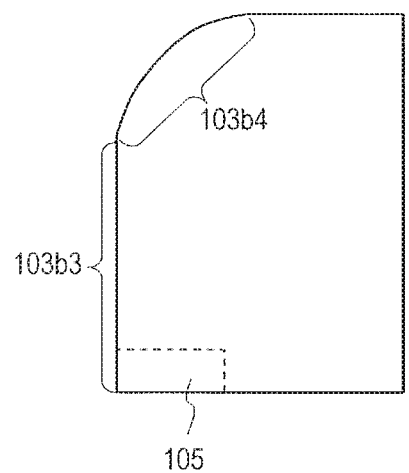
FIG. 10A A diagram explaining another exemplary shape of a side face portion of the first chamber, in a cross section taken parallel to the radial direction.
Figure 10B:
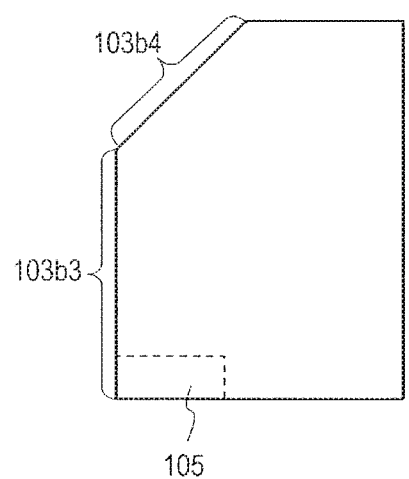
FIG. 10B A diagram explaining another exemplary shape of a side face portion of the first chamber, in a cross section taken parallel to the radial direction.
Figure 10C:
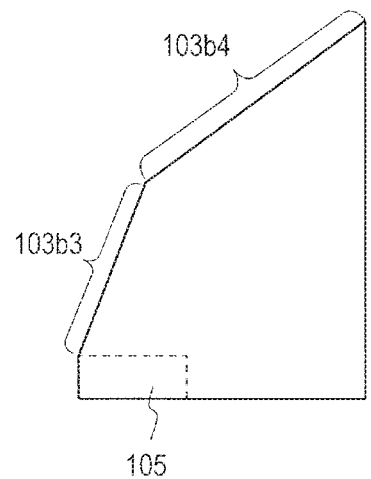
FIG. 10C A diagram explaining another exemplary shape of a side face portion of the first chamber, in a cross section taken parallel to the radial direction.

FIG. 10A to FIG. 10C show variations of shapes of the side face portion 103b in a cross section which is parallel to a radial direction from the rotation axis 101 and is perpendicular to the principal face 100m.

FIG. 10A shows an example where $\alpha_1 = \alpha_2 = \alpha_3 = \ldots = \alpha_h = 0$ in the third side face subportion 103b3. FIG. 10B and FIG. 10C show examples where $\alpha_1 = \alpha_2 = \alpha_3 = \ldots = \alpha_h < \alpha_{h+1} = \ldots = \alpha_n$ in expression (1). In FIG. 10B in particular, $\alpha_1 = \alpha_2 = \alpha_3 = \ldots = \alpha_{h=3}$.

Figure 11A:
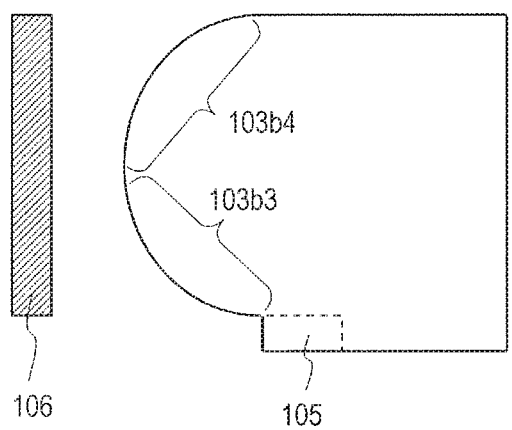
FIG. 11A A diagram explaining another exemplary shape of a side face portion of the first chamber, in a cross section taken parallel to the radial direction.
Figure 11B:
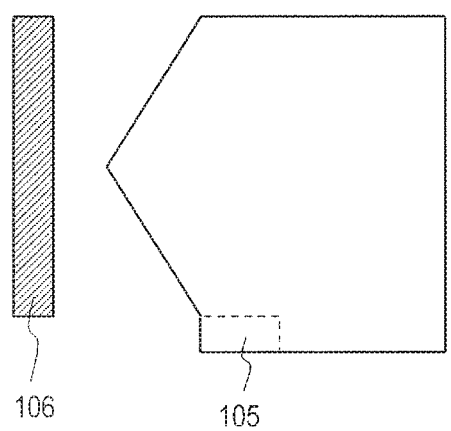
FIG. 11B A diagram explaining another exemplary shape of a side face portion of the first chamber, in a cross section taken parallel to the radial direction.

The side face portion 103b may have still other shapes in a cross section which is parallel to a radial direction from the rotation axis 101 and is perpendicular to the principal face 100m. As shown in FIG. 11A and FIG. 11B, in a cross section which is parallel to a radial direction from the rotation axis 101 and is perpendicular to the principal face 100m, the side face portion 103b may have a recess which is dented away from the rotation axis 101, i.e., a protrusion protruding toward the magnet 106. In a cross section which is parallel to a radial direction from the rotation axis 101 and is perpendicular to the principal face 100m, the third side face subportion 103b3 and the fourth side face subportion 103b4 of the side face portion 103b shown in FIG. 11A together present an arc shape. The third side face subportion 103b3 and the fourth side face subportion 103b4 of the side face portion 103b as shown in FIG. 11B present a V-shape as viewed from the rotation axis 101 side.

(Construction and Variants of the Magnet 106)

Figure 12:
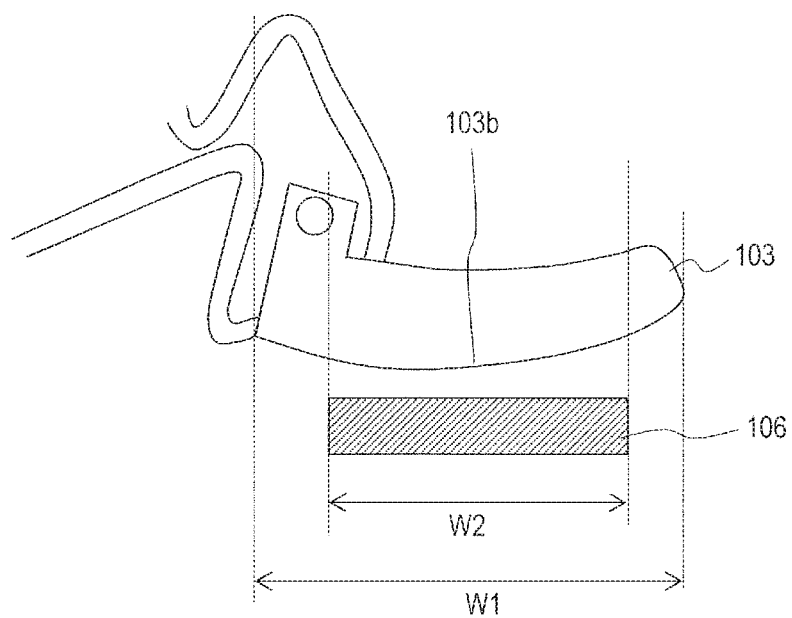
FIG. 12 A diagram showing an exemplary relationship between width of the first chamber and width of the magnet as viewed from a direction which is perpendicular to a principal face.

Hereinafter, construction and variants of the magnet 106 will be described. As described earlier, since the magnetic particles 311 are to be captured with the magnet 106, that the magnet 106 is preferably not near the opening of the channel 105. In the present embodiment, as shown in FIG. 12, the channel 105 is provided at one end E1 of the side face portion 103b as viewed from a plane which is perpendicular to the principal face 100m of the substrate 100 for sample analysis. In this case, the width W2 of the magnet 106 is preferably shorter than the width W1 of the side face portion 103b.

Moreover, preferably, the magnet 106 is at least distant from the one end E1 of the side face portion 103b at which the channel 105 is provided. As a result of this, the magnetic particles 311 which are attracted to the magnet 106 may be captured in the region between both ends E1 and E2 of the side face portion 103$b$, both ends E1 and E2 being excluded.

Figure 13A:
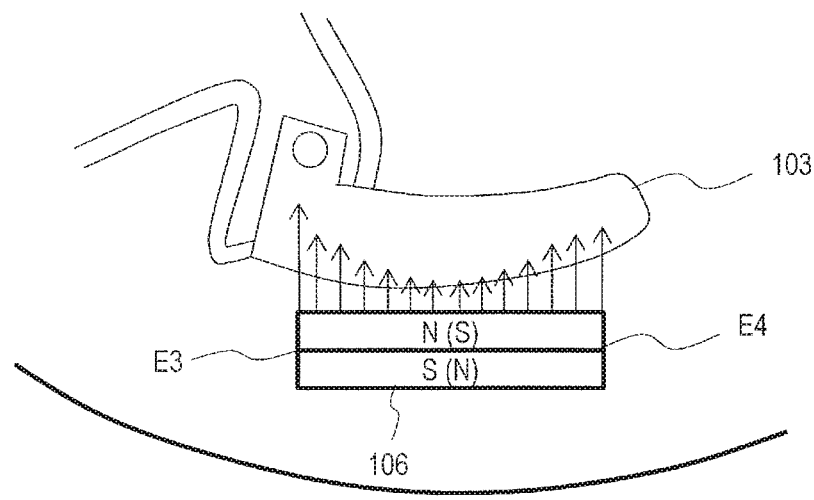
FIG. 13A A schematic diagram showing an example of magnet construction and magnetic force magnitudes.
Figure 13B:
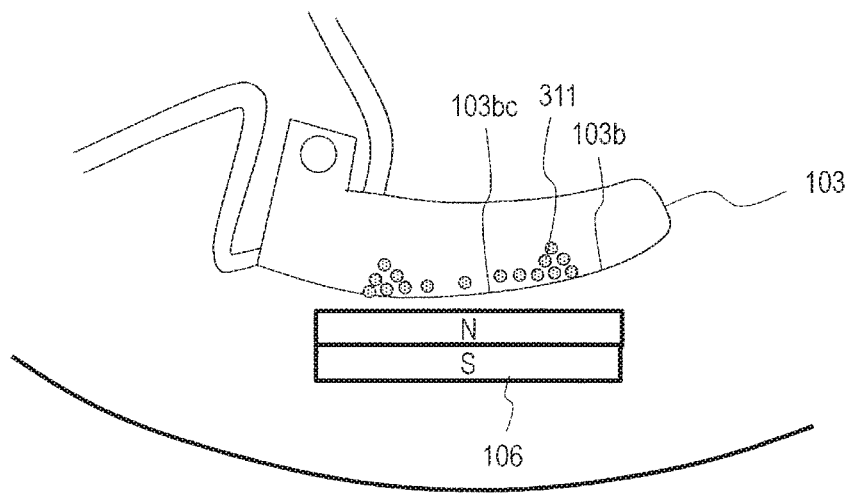
FIG. 13B A schematic diagram showing an exemplary distribution of composite, given the exemplary magnet construction shown in FIG. 13A.

As shown in FIG. 13A, the magnet 106 may have its different magnetic poles along a radial direction from the rotation axis 101 as viewed from a plane which is perpendicular to the principal face 100$m$ of the substrate 100 for sample analysis, for example. In this case, as shown in FIG. 13A, near both ends E3 and E4 of the magnet 106, the magnetic flux density increases, resulting in a large magnetic force. Therefore, as shown in FIG. 13B, the magnetic particles 311 are captured in regions that are distant from the center 103$bc$ of the side face portion 103$b$, toward both ends E3 and E4. In this case, too, if the width W2 of the magnet 106 is shorter than the width W1 of the side face portion 103$b$, the captured magnetic particles 311 are relatively distant from the opening of the channel 105. Therefore, it is unlikely for the magnetic particles 311 that have been captured by the magnet 106 to flow into the channel 105.

Figure 14A:
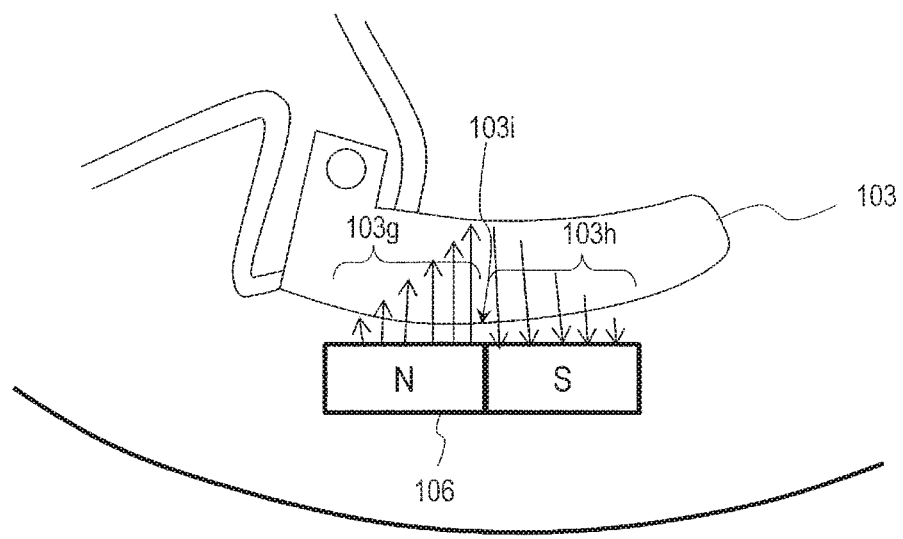
FIG. 14A A schematic diagram showing another example of magnet construction and magnetic force magnitudes.

In order to capture the magnetic particles 311 at the center of the side face portion 103$b$, as shown in FIG. 14A, the magnet 106 may be configured so that the magnetic flux density at both ends E3 and E4 of the side face portion 103$b$ is smaller than the magnetic flux density at portions of the side face portion 103$b$ other than both ends E3 and E4, as viewed from a direction which is perpendicular to the principal face 100$m$.

Figure 14B:
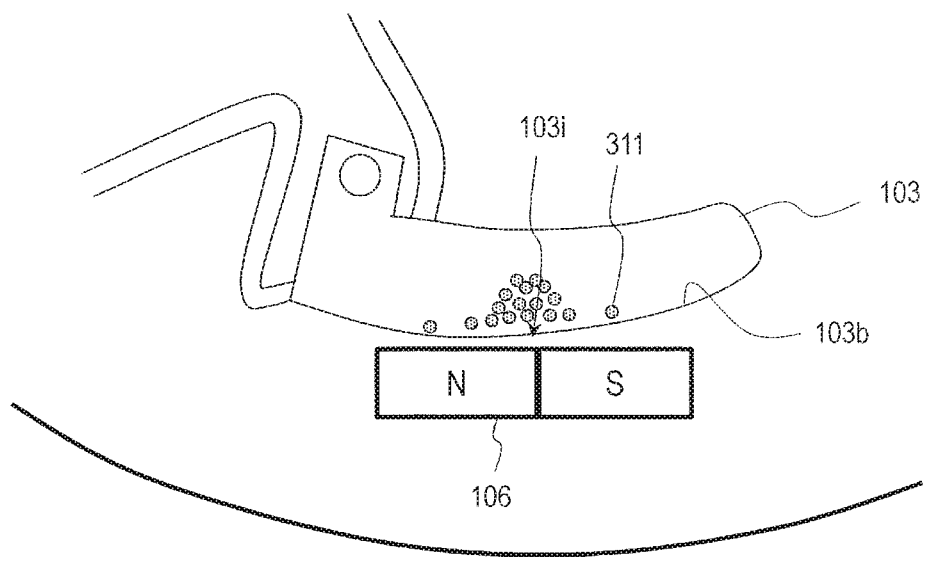
FIG. 14B A schematic diagram showing an exemplary distribution of composite, given the exemplary magnet construction shown in FIG. 14A.

For example, when the side face portion 103$b$ is split into two at an arbitrary position 103$i$ as viewing the side face portion 103$b$ from a direction which is perpendicular to the principal face 100$m$, the magnet 106 has an N pole in its portion corresponding to one of the split portions 103$g$ and an S pole in its portion corresponding to the other split portion 103$h$. By thus placing the two magnetic poles, as shown in FIG. 14A, the magnetic flux density increases near the split position 103$i$. Therefore, as shown in FIG. 14B, a large number of magnetic particles 311 are gathered near the position 103$i$. Moreover, since the flux path length becomes shorter, leakage of magnetic flux to the exterior can be suppressed.

Figure 15:
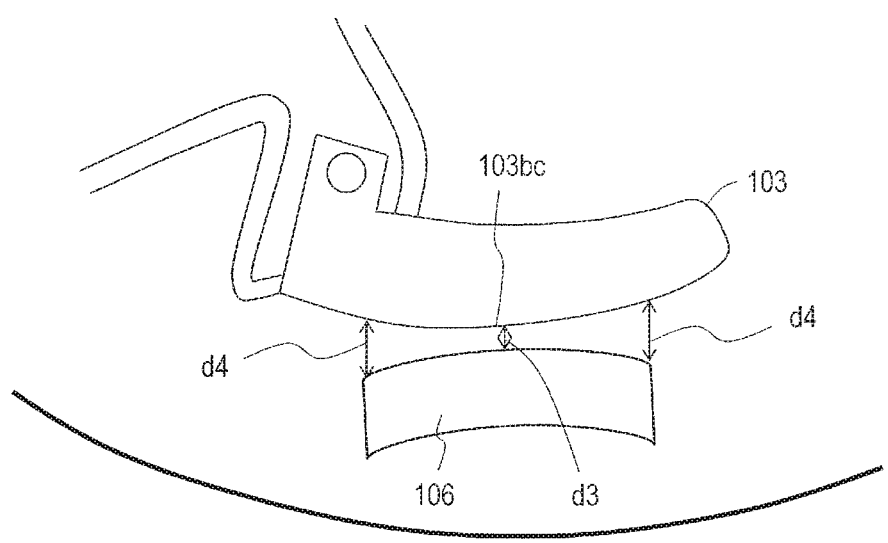
FIG. 15 A schematic diagram showing another exemplary magnet construction.

Moreover, as shown in FIG. 15, a magnet 106' having a bow shape protruding toward the rotation axis 101, as viewed from a direction which is perpendicular to the principal face 100$m$, may be disposed near the side face portion 103$b$. The magnet 106' has its different magnetic poles along the radial direction. Since the magnet 106' has a bow shape, the distance d4 to the side face portion 103$b$ at both ends of the magnet 106' is longer than the distance d3 to the side face portion 103$b$ at the center of the magnet 106'. Therefore, the magnetic flux density at the ends is smaller than at the central portion of the side face portion 103$b$, so that a large number of magnetic particles 311 are gathered near the central portion.

(Other Examples of the Substrate 100 for sample Analysis and the Sample Analysis Device)

In the present embodiment, the substrate 100 for sample analysis includes the magnet 106 being inserted in the substrate 100'. However, the magnet may be provided in the sample analysis device 200. The following constructions may be possible in the case where the sample analysis device 200 includes the magnet 106, for example.

A first example where the sample analysis device 200 includes the magnet 106 will be described. For example, the substrate 100' of the substrate 100 for sample analysis may have the receptacle 120 as has been described with reference to FIG. 3C. On the other hand, the sample analysis device 200 includes a driving mechanism which inserts the magnet 160 in the receptacle 120 of the substrate 100 for sample analysis being placed on the turntable 201$a$, and removes the magnet 160 from the substrate 100 for sample analysis. The driving mechanism is a robot arm, for example.

Under the control of the control circuit 205 shown in FIG. 2A, while rotation of the substrate 100 for sample analysis placed on the turntable 201$a$ is stopped, the driving mechanism inserts the magnet 106 into the receptacle 120, and removes the magnet 106 in the receptacle 120.

Figure 16A:
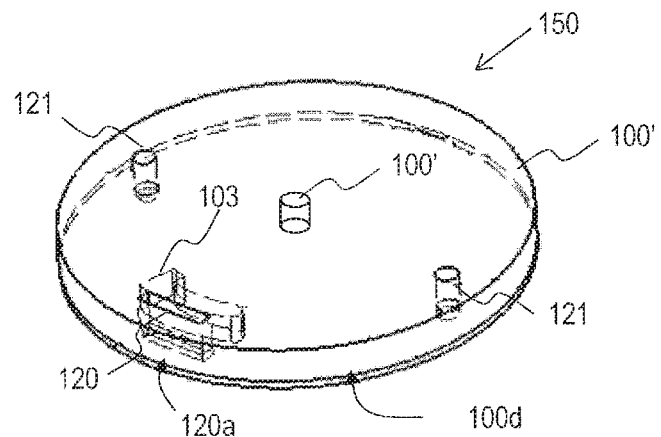
FIG. 16A A perspective view showing another exemplary structure of a substrate for sample analysis.

A second example where the sample analysis device 200 includes the magnet 106 will be described. In the second example, the magnet 106 is attached to the turntable which supports the substrate 100 for sample analysis. FIG. 16A is a perspective view of a substrate 150 for sample analysis. The substrate 150 for sample analysis shown in FIG. 16A includes a substrate 100'. Inside the substrate 100', the substrate 100' has a receptacle 120 near the first chamber 103. In the example shown in FIG. 16A, the receptacle 120 is more distant from the rotation axis 101 than is the first chamber 103. The receptacle 120 has an opening 120$a$ in the principal face 100$d$. Moreover, the substrate 100' has two engagement holes 121 with their openings in the principal face 100$d$.

Figure 16B:
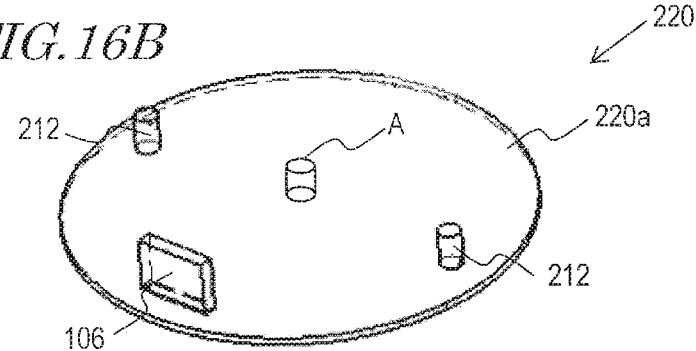
FIG. 16B A perspective view showing an exemplary structure of an auxiliary turntable which is used for the substrate for sample analysis shown in FIG. 16A.

FIG. 16B is a perspective view of an auxiliary table 220 to be attached to the turntable 201$a$ of the sample analysis device 200 shown in FIG. 2A. As the auxiliary table 220 is attached to the turntable 201$a$, the auxiliary table 220 and the turntable 201$a$ integrally function as a turntable. The auxiliary table 220 has a bearing surface 220$a$ on which to support the substrate 100 for sample analysis and a magnet 160 protruding from the bearing surface 220$a$. It also includes two engaging pins 212 protruding from the bearing surface 220$a$. On the bearing surface 220$a$, the engaging pins 212 and the magnet 160 are disposed at positions for insertion into the engagement holes 121 and the receptacle 120, respectively, in a state where the auxiliary table 220 is supporting the substrate 150 for sample analysis. They are located on the bearing surface 220$a$.

Figure 16C:
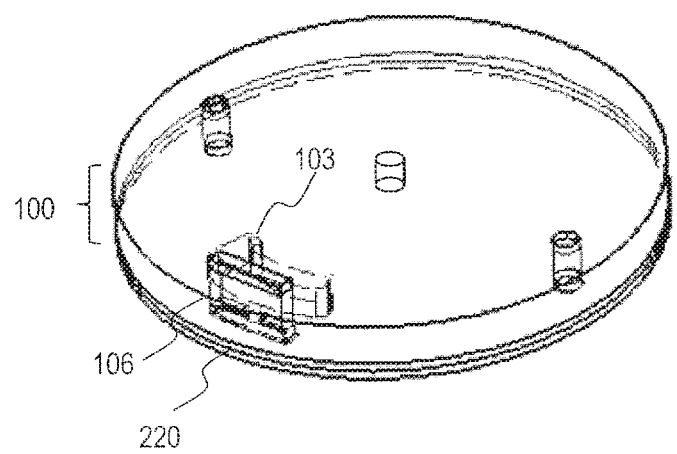
FIG. 16C A perspective view showing an exemplary state where the substrate for sample analysis shown in FIG. 16A is attached to the auxiliary turntable shown in FIG. 16B.

The bearing surface 220$a$ of the auxiliary table 220 attached to the turntable 201$a$ and the principal face 100$d$ of the substrate 150 for sample analysis are allowed to face each other; the engaging pins 212 and the magnet 106 are respectively aligned with the engagement holes 121 and the receptacle 120; and the substrate 150 for sample analysis is attached to the auxiliary table 220, i.e., the turntable. As a result of this, the engaging pins 212 and the magnet 106 become inserted into the engagement holes 121 and the receptacle 120, respectively, and as shown in FIG. 16C, the substrate 150 for sample analysis becomes placed on the auxiliary table 220. In this state, with reference to FIG. 3A, among the inner surfaces defining the first space of the first chamber 103 in the substrate 100 for sample analysis, it is disposed at the side face portion that is the farthest from the rotation axis 101. As a result, the magnet 106 is disposed near the side face portion 103$b$ that is the farthest from the rotation axis 101, thereby being able to capture the magnetic particles at the side face portion 103$b$.

Note that the positions of the receptacle 120 and the magnet 106 as shown in FIG. 16A to FIG. 16C are examples; these positions may change depending on the position of the first chamber 103. Moreover, in the case where the first chamber is located near the outer periphery of the substrate 150 for sample analysis, for example, an auxiliary table 220 which is larger than the substrate 150 for sample analysis may be used, and the magnet 106 may be provided on the auxiliary table 220 so that the magnet 106 is located by a side face of the substrate 150 for sample analysis, which is placed on the auxiliary table 220. In this case, the substrate 150 for sample analysis does not need the receptacle 120. Moreover, the auxiliary table 220 and the turntable 201a may be formed as an integral piece, and an electromagnet may be used as the magnet 160.

INDUSTRIAL APPLICABILITY

The substrate for sample analysis and sample analysis device sample analysis system disclosed in the present application are applicable to the analysis of a specific component within an analyte via various reactions.

REFERENCE SIGNS LIST

100 substrate for sample analysis
100' substrate
100a base substrate
100b cover substrate
100m principal face
101 rotation axis
102 reaction chamber
103 first chamber
103a, 103b, 103c, 103d side face portion
103b1 first side face subportion
103b2 second side face subportion
103b3 third side face subportion
103b4 fourth side face subportion
103bc center
103e upper face portion
103f lower face portion
103g split portion
103h split portion
104, 105 channel
106, 106' magnet
107 second chamber
107a side face portion
108 air hole
109 opening
110 liquid
110s liquid surface
130b side face portion
200 sample analysis device
201 motor
201a turntable
203 origin detector
204 rotation angle detection circuit
205 control circuit
206 drive circuit
207 optical measurement unit
302 magnetic particles
304 primary antibody
305 magnetic-particle-immobilized antibody
306 antigen
307 label substance
308 labeled antibody
310 composite
501 sample analysis system

The invention claimed is:

1. A sample analysis system comprising:
   a substrate for sample analysis on which transfer of a liquid is to occur with rotational motion, the substrate for sample analysis comprising:
      a substrate having a rotation axis;
      a first chamber being located in the substrate and having a first space for retaining a liquid and magnetic particles;
      a second chamber being located in the substrate and having a second space for retaining the liquid to be discharged from the first chamber;
      a channel being located in the substrate and having a path connecting the first chamber and the second chamber; and
      a magnet being located, in the substrate, outside the first space in the radial direction from the rotation axis, a location of the magnet allowing the magnet to attract the magnetic particles to be captured in the first chamber; and
   a sample analysis device including:
      a motor to rotate the substrate for sample analysis around the rotation axis in a state where the rotation axis is at an angle which is not less than 0° and not more than 90° with respect to the direction of gravity,
      a rotation angle detection circuit to detect a rotation angle of a shaft of the motor,
      a drive circuit to control rotation of the motor and a rotation angle of the motor when stopped based on a result of detection by the rotation angle detection circuit, and
      a control circuit including an arithmetic unit, a memory, and a program which is stored in the memory and executable by the arithmetic unit, to control based on the program an operation of the motor, the rotation angle detection circuit, and the drive circuit,
   wherein,
   when the substrate for sample analysis with the first chamber being filled with a liquid containing magnetic particles is mounted to the sample analysis device,
      (a) as the substrate for sample analysis is stopped at a predetermined rotation angle, the channel becomes filled with a portion of the liquid in the first chamber via capillary action, and
      (b) as the substrate for sample analysis is rotated at a rate causing a centrifugal force which is stronger than a capillary force acting on the liquid filling the channel, the liquid in the first chamber is moved through the channel to the second chamber while the magnetic particles are captured in the first chamber with the magnet.

2. A sample analysis device, suitable for a substrate for sample analysis which includes a substrate having a rotation axis and a plate shape with a predetermined thickness, a first chamber being located in the substrate and having a first space for retaining a liquid and magnetic particles, and a receptacle located, in the substrate, outside the first space in the radial direction from the rotation axis, wherein transfer of a liquid is to occur with rotational motion, the sample analysis device comprising:
   a motor to rotate the substrate for sample analysis around the rotation axis in a state where the rotation axis is inclined at an angle which is not less than 0 degrees and not more than 90 degrees with respect to the direction of gravity;
   a rotation angle detection circuit to detect an angle of a shaft of the motor;
   a drive circuit to control rotation and a stopping angle of the motor based on a result of detection by the angle detector;
   a magnet;

a driving mechanism to, while rotation by the motor is stopped, insert the magnet into the receptacle of the substrate for sample analysis and remove the magnet in the receptacle; and a controller circuit to control an operation of the motor, the rotation angle detection circuit, the drive circuit, and the driving mechanism.

3. A sample analysis device, suitable for a substrate for sample analysis which includes a substrate having a rotation axis and a plate shape with a predetermined thickness, a first chamber being located in the substrate and having a first space for retaining a liquid and magnetic particles, and a receptacle being located, in the substrate, outside the first space in the radial direction from the rotation axis and having an opening in a principal face of the substrate, wherein transfer of a liquid is to occur with rotational motion, the sample analysis device comprising:

a turntable having a rotation axis, a bearing surface to support the substrate for sample analysis, and a magnet protruding from the bearing surface and being disposed at a position for insertion into the receptacle of the substrate for sample analysis supported on the bearing surface;

a motor to rotate the turntable around the rotation axis in a state where the rotation axis of the turntable is inclined at an angle which is not less than 0 degrees and not more than 90 degrees with respect to the direction of gravity;

an angle detector to detect an angle of a shaft of the motor;

a drive circuit to control rotation and a stopping angle of the motor based on a result of detection by the angle detector; and a control circuit to control an operation of the motor, the angle detector, and the drive circuit.

* * * * *